US006630178B1

(12) United States Patent
Høie

(10) Patent No.: US 6,630,178 B1
(45) Date of Patent: Oct. 7, 2003

(54) COMPOSITION COMPRISING SOY PROTEIN, DIETARY FIBRES AND A PHYTOESTROGEN COMPOUND AND USE THEREOF IN THE PREVENTION AND/OR TREATMENT OF CARDIOVASCULAR DISEASES

(75) Inventor: Lars Henrik Høie, London (GB)

(73) Assignee: Nutri Pharma Asa, Oslo (NO)

( * ) Notice: Subject to any disclaimer, the term of this patent is extended or adjusted under 35 U.S.C. 154(b) by 0 days.

(21) Appl. No.: 09/856,883

(22) PCT Filed: Nov. 25, 1999

(86) PCT No.: PCT/IB99/01998

§ 371 (c)(1),
(2), (4) Date: Aug. 13, 2001

(87) PCT Pub. No.: WO00/30665

PCT Pub. Date: Jun. 2, 2000

(30) Foreign Application Priority Data

Dec. 25, 1998 (DK) ............................................. 98 01555
Jun. 16, 1999 (DK) ............................................. 99 00855

(51) Int. Cl.[7] ........................ A61K 35/78; A61K 47/00
(52) U.S. Cl. ....................................... 424/757; 424/439
(58) Field of Search ................................ 424/757, 439, 424/400; 514/2, 909, 824

(56) References Cited

U.S. PATENT DOCUMENTS

| | | | |
|---|---|---|---|
| 4,557,927 A | 12/1985 | Miyake et al. |
| 4,591,600 A | 5/1986 | Creuzet et al. |
| 4,818,558 A | 4/1989 | Hartman et al. |
| 4,841,077 A | 6/1989 | Ito et al. |
| 4,960,908 A | 10/1990 | Ito et al. |
| 5,320,949 A | 6/1994 | Shen |
| 5,352,384 A | 10/1994 | Shen |
| 5,498,631 A | 3/1996 | Gorbach et al. |
| 5,516,528 A | 5/1996 | Hughes et al. |
| 5,589,182 A | 12/1996 | Tashiro et al. |
| 5,637,561 A | 6/1997 | Shen et al. |
| 5,637,562 A | 6/1997 | Shen et al. |
| 5,654,011 A | 8/1997 | Jackson et al. |
| 5,698,256 A | 12/1997 | Stilling |
| 5,702,752 A | 12/1997 | Gugger et al. |
| 5,855,892 A | 1/1999 | Potter et al. |
| 6,326,031 B1 * | 12/2001 | Hsia et al. |
| 6,509,043 B1 * | 1/2003 | Hoie |

FOREIGN PATENT DOCUMENTS

| | | | |
|---|---|---|---|
| CN | 1102991 | * | 5/1995 |
| EP | 0827698 | | 9/1997 |
| EP | 0898900 | | 3/1998 |
| EP | 0647408 | | 12/1999 |
| FR | 2395288 | | 6/1977 |
| JP | 1258669 | | 4/1988 |
| JP | 08064368 | | 3/1996 |
| WO | WO 93 23069 | | 5/1993 |
| WO | WO 95 10512 | | 9/1994 |
| WO | WO 95 10529 | | 9/1994 |
| WO | WO 95 10530 | | 9/1994 |
| WO | WO 96 10341 | | 10/1995 |
| WO | WO 97 07811 | | 8/1996 |
| WO | WO 97 31546 | | 2/1997 |
| WO | WO 97 37547 | | 4/1997 |
| WO | WO 98 03084 | | 7/1997 |

OTHER PUBLICATIONS

*A Review of the Clinical Effects of Phytoestrogens,* Knight and Eden, Obstetrics & Gynecology, vol. 87, No. 5, Part 2, pp 897–904, May 1996.
*A Soy Protein Isolate Rich in Genistein and Daidzein and Its Effects on Plasma Isoflavone Concentrations, Platelet Aggregation, Blood Lipids and Fatty Acid Composition of Plasma Phospholipid in Normal Men,* Gooderham, et al., J. Nutrition, vol. 126/8, pp. 2000–2006 (1986).
*Defining Food Components and New Nutrients,* Hendrich et al., J. Nutr. 124: 1789S–1789S, 1994.
*Depression of plasma cholesterol in men by consumption of baked products containing soy protein,* Potter, et al., American Journal of Clinical Nutrition 58 (1993): 4 (Oct.)
*Effects of Tyrosine Kinase Inhibitors on Antigen Challenge of Guinea Pig Lung in Vitro,* Wong, et al., The Journal of Pharmacology and Experimental Therapeutics, vol. 283, No. 1, 1997, pp. 131–137.
*Intake of 25g of Soybean Protein with or without Soybean Fiber Alters Plasma Lipids in Men with Elevated Cholesterol Concentrations,* Bakhit, et al., J. Nutr. 124: 213–222, 1994.
*Lipoprotein Heterogeneity and Apolipoprotein B Metabolism,* Packard and Shepard, Arteriosclerosis, Thrombosis, and Vascular Biology, vol. 17, No. 12, Dec. 1997, pp 3542–3556.
*Long–Term Treatment of Hypercholesterolemia With Dietary Fiber,* Hunninghake, et al., The American Journal of Medicine, vol. 97, pp 504–508, Dec. 1994.

(List continued on next page.)

Primary Examiner—Christopher R. Tate
Assistant Examiner—Michele C. Flood
(74) Attorney, Agent, or Firm—Gabor L. Szekeres

(57) ABSTRACT

A composition comprising (a) soy protein, (b) a phytoestrogen compound, and (c) dietary fibers. The soy protein (a) is present in an amount of at least 45 weight percent of the total protein content of the composition, said total protein content providing at least 15 percent of the total energy content of the composition. The phytoestrogen compound (b) is preferably a naturally occuring isoflavone and is present in an amount of more than 0.10 weight percent of the soy protein, and the dietary fibers (c) are preferably soybean fibers and are present in an amount of more than 4 weight percent of the total weight of the nutritional composition on a dry basis. The composition is useful in lowering serum cholesterol and LDL-cholesterol and serum triglyceride levels and for increasing the HDL/LDL-cholesterol ratio in serum of a subject suffering from arteriosclerosis and related cardiovascular diseases.

46 Claims, 5 Drawing Sheets

OTHER PUBLICATIONS

*Meta–analysis of the Effects of Soy Protein Intake on Serum Lipids*, Anderson, et al., The New England Journal of Medicine, vol. 333, No. 5, pp 276–282, Aug. 3, 1995.

*Modern Applications for an Ancient Bean: Soybeans and the Prevention and Treatment of Chronic Disease*, Messina, J. Nutr. 125: 567S–569S, 1995.

*New Trends in Atherosclerotic Research*, Faggiotto, Atherosclerosis Reviews, vol. 21, pp 187–194 (1990).

*Phytoestrogen Content of Foods—A Compendium of Literature Values*, Reinli and Block, Nutrition and Cancer 1996.

*Phytoestrogens—a short review*, Knight and Eden, Maturitas 22, Journal of the Climacteric and Postmenopause, pp 167–175 (1995).

*Phyto–oestrogens and Western Diseases*, Adlecreutz and Mazur, The Finnish Medical Society DUODECIM, Ann. Med. 29, 95–120 (1997).

*Putting Low–Density Lipoproteins at Center Stage in Atherogenesis*, Sniderman, et al., The American Journal of Cardiology, vol. 79, Jan. 1, 1997.

*Soy Containing Isolflavones Reduces Cholesterol*, Crouse and Burke, Abstract for presentation at the American Heart Association, Mar. 1998.

*Soy isoflavones enhance coronary vascular reactivity in atherosclerotic female macaques*, Honore et al, Fertility and Sterility, vol. 67, No. 1, pp. 148–154 (Jan. 1997).

*Soy: is this a food we could be encouraging in diabetes?*, Govindji, Practical Diabetes International, vol. 15, No. 6, Sep. 1998, pp. 163–164.

*Soy protein and serum lipids*, Potter, Current Opinion in Lipidology 1996, 7, pp. 260–264.

\* cited by examiner

COMPOSITION COMPRISING SOY PROTEIN, DIETARY FIBRES AND A PHYTOESTROGEN COMPOUND AND USE THEREOF IN THE PREVENTION AND/OR TREATMENT OF CARDIOVASCULAR DISEASES

FIELD OF THE INVENTION

The present invention relates to soy protein, phytoestrogens and dietary fibres and compositions thereof suitable for preventing, alleviating and/or treating cardiovascular diseases such as arteriosclerosis, hypercholesterolemia, hyperlipidemia, hypertriglyceridemia, hypertension and related cardiovascular diseases. In particular a composition according to the present invention has improved effects in lowering levels of total serum cholesterol and LDL-cholesterol. A composition according to the present invention is also particularly useful in reducing the accumulation of cholesterol in the arterial wall of subjects at high risk for developing cardiovascular disease or already suffering from a cardiovascular disease such as atherosclerosis. A composition according to the present invention is also useful for lowering serum levels of total cholesterol and/or LDL-cholesterol and/or triglycerides and/or homocystein and/or for increasing serum levels of HDL-cholesterol and/or for improving the HDL/LDL-ratio in subjects at risk for developing cardiovascular diseases and in subjects already suffering from an arteriosclerotic condition such as e.g. atherosclerosis or a related cardiovascular disease. The present invention also relates to the use of these compositions in the manufacture of a medicament for treating a subject suffering from cardiovascular diseases, more particularly arteriosclerosis, hypercholesterolemia, hyperlipidemia, hypertriglyceridemia, hypertension and/or related cardiovascular diseases. The present invention also concerns use of a composition according to the present invention in the prevention and/or treatment of said diseases and disorders and for lowering serum levels of total cholesterol and/or LDL-cholesterol and/or triglycerides and/or serum levels of homocystein in subjects. In addition, the present invention also provides methods for preventing and/or treating and/or prophylactically treating and/or alleviating by therapy said diseases and disorders.

BACKGROUND OF THE INVENTION

Lipid metabolism involves biosynthesis and degradation of e.g. fatty acids, triglycerides and cholesterol. Ingested triglycerides are hydrolysed in the small intestine and hydrolysis products are absorbed by the intestinal mucosa. Due to the relative insolubility of dietary lipids in water, lipid digestion and absorption is facilitated by the action of detergent substances such as bile acids secreted from the gallbladder. Bile acids are essential for lipid digestion and absorption through the intestinal mucosa.

Triglycerides and cholesterol synthesized in the liver are transported in the bloodstream to peripheral tissues by transport proteins called lipoproteins. Lipoproteins are tiny vesicles coated by apoproteins, phospholipids and free cholesterol and with an interior consisting of the more hydrophobic lipids, cholesteryl esters and triglycerides. Apoproteins and lipoproteins are primarily synthesized in the liver. The lipoproteins are capable of performing an apoprotein mediated binding to a receptor on the surface of a cell into which the entire lipoprotein particle is taken up and further metabolised.

Several different families of lipoproteins have been characterized and are traditionally classified by their density as determined by centrifugation. A standard lipoprotein classification scheme may include in increasing order of density, very low-density lipoprotein (VLDL), intermediate-density lipoprotein (IDL), low-density lipoprotein (LDL), and high-density lipoprotein (HDL).

VLDL contains approximately 60 to 65 percent triglycerides and 5 to 10 percent cholesterol, lecithin and protein. They are relatively large and function in the transport of triglycerides from the liver to tissue. LDL contains approximately 40 to 50 percent cholesterol and 10 to 15 percent triglycerides, lecithin and protein. They are somewhat smaller than VLDL and also function in the transport of cholesterol from the liver to tissue. HDL contains roughly 75 percent lecithin and protein, while the rest is made up of cholesterol and a small amount of triglycerides. They function in the transport of cholesterol from tissue to the liver and, as such, have the opposite function of LDL. Cholesterol esters cannot readily traverse cellular membranes and are taken up by cells in a receptor-mediated process. Once bound to the LDL-receptor, the LDL-particle is internalised by means of endocytosis, and cholesterol and fatty acids are released and further metabolised.

Ongoing investigations of the LDL-receptor-mediated internalization of cholesterol have generated a better understanding of the relationship between dietary cholesterol, plasma cholesterol levels, and the condition of artherosclerosis. It is believed that the white blood cells that accumulate cholesterol at sites of arterial injury contain a receptor termed a scavenger receptor. Like the LDL-receptor, this scavenger receptor acts by the mechanism of endocytosis and mediates internalization of various extracellular materials. However, the scavenger receptor is indiscriminatory and takes up many different types of extracellular materials including oxidized-LDL-particles containing cholesterol. In contrast to the LDL-receptor, the scavenger receptor is not down-regulated by a high concentration of cholesterol in the cell.

In addition to the above-mentioned lipoproteins, the organism also contains a type of lipoproteins called chylomicrons. Chylomicrons contain 90 to 95 percent triglycerides and only a small amount of cholesterol, lecithin and protein, and they function in the transport of triglycerides from the small intestine to e.g. muscles, liver and heart.

The metabolism of cholesterol in the human organism is closely linked to the synthesis, transport and degradation of triglycerides. Cholesterol is an essential lipid component in all mammalian cells. It is used to regulate the fluidity of cellular membranes and serves as a precursor for certain hormones, vitamin D and bile acids. Cholesterol is synthesized in the liver and is transported with the blood to peripheral tissues by lipoproteins. The liver has a dual function in the metabolism of cholesterol since it is capable of both synthesizing cholesterol and converting surplus cholesterol into bile acids. It is also capable of excreting cholesterol into the bile.

Bile acids have ampholytic characteristics and contain both hydrophobic and hydrophilic surfaces. This ampholytic character facilitates a bile acid mediated emulsification of lipids into micelles. The formation of micelles allows digestive attacks by water-soluble enzymes and facilitates lipid absorption through the mucosal cells of the intestine. Bile acids are secreted from the liver and stored in the gallbladder before being passed through the bile duct and into the intestine. Biosynthesis of bile acids represents a major metabolic fate of cholesterol and accounts for more than half of the approximately 800 mg cholesterol that is normally metabolised per day in a normal adult. Even though bile acids in an amount of 400 mg are synthesized each day, significantly more than this amount is secreted into the intestine. Most of the bile acids that are secreted into the upper small intestine are absorbed in the lower small intestine and are recycled to the liver. The process of enterohepatic circulation may amount to as much as 20 to 30 g of bile acids per day. In contrast, daily elimination of bile acids in the faeces amounts to just 0.5 g or less.

Cholesterol acts on three different levels of regulation of its own synthesis. Firstly, it suppresses endogenous cholesterol synthesis by inhibiting HMG-CoA reductase. Secondly, it activates acyl-CoA:cholesterol acyltransferase (ACAT) which is involved in the synthesis of cholesterol esters from cholesterol and fatty acids bound to acyl-CoA. Thirdly, cholesterol regulates synthesis of the LDL-receptor. Accordingly, a decreased synthesis of LDL-receptors will ensure that a cell in which a sufficient amount of cholesterol is already present does not take up cholesterol. This may explain why excessive dietary cholesterol generates a rapid elevation of cholesterol levels in the blood.

The presence of increased amounts of cholesterol in the blood is known to be positively correlated to arteriosclerosis, a condition commonly attributed to the deposition on the inner lining of an arterial wall of plaque in the form of cholesterol and fats. One commonly occurring arterial condition is that of atherosclerotic cardiovascular disease. The condition may eventually progress through several stages. A normal structure of an artery is characterized by discrete focal numbers of adhering monocytes, some intimal foam cells, and some intimal smooth muscle cells, or intimal cell masses at bifurcations. A fatty streak may occur non-symptomatically and involve a layer of foam cells. As arteriosclerosis progresses, the arterial wall will gradually start to harden due to the deposition of lipid and calcium and proliferation of smooth muscle cells, and the cells may eventually become degenerated. As the wall of an artery thickens, hardens, and lose its elasticity during arteriosclerosis, the blood vessels may develop twists and turns and become narrowed so that the heart must work harder to pump the usual amount of blood through the arteries. The condition may progress into a formation of e.g. fibrous plaque. Fibrous plaque is a slowly reversible condition that may develop further into a complicated lesion.

Cellular degeneration is likely to result in a fracture of the arterial wall which in turn leads to the formation of a deposit of calcium, platelet formation and a gradual development of scar tissue that further contributes to cellular degeneration and a substantially reduced elasticity of the arterial wall. Atherosclerosis characterised by a restricted flow of blood through a coronary artery may lead to the development of coronary heart disease, A complicated lesion of an artery is often symptomatic, hardly reversible and may, in severe cases such as thrombosis, be lethal. A decreased flow of blood through an artery may lead to the formation of blood clots and this may eventually lead to thrombosis. If a blood clot forms in a coronary artery, the interruption of the blood flow may result in the death of part of the heart muscle and cause the extremely painful chest pains associated with a heart attack.

Arteriosclerotic symptoms largely depend on the arteries and tissue affected. When arteriosclerosis occurs in the arteries leading to the brain, the decrease in blood flow and oxygen can cause mental confusion and personality changes. A stroke may occur, if an artery in the brain that has been weakened by a rupture or a blood clot prevents blood from flowing to the brain. This may possibly result in e.g. partial paralysis, loss of speech, and sometimes even death. A decrease in the flow of blood through the coronary arteries results in a shortage of oxygen to the heart muscle and causes chest pains and a painful condition called angina pectoris. Angina pectoris is usually caused by a narrowing or an obstruction of a coronary artery. An attack of angina pectoris may be caused by stress or result from physical activities that require an increased supply of blood to the heart.

Although it is well established that cholesterol, lipids and lipoproteins all contribute to the progression of various arteriosclerotic conditions, little is known about the causes of arteriosclerosis. Hereditary conditions clearly play a role in some cases and several socio-economical and life style related factors such as smoking, hypertension, dietary habits and continual stress also contribute to the development of arteriosclerosis.

There is at present no simple cure or medical treatment for arteriosclerosis and doctors usually advise patients to follow a low fat diet, to stop smoking and to exercise regularly. Patients suffering from hypercholesterolemia may be classified into four risk groups: (i) manifest coronary artery disease, (ii) other forms of atherosclerotic vascular disease, (iii) other risk factors for coronary artery disease in the absence of established atherosclerotic cardiovascular disease, and (iv) isolated hypercholesterolemia in the absence of other risk factors. The recommended treatment regimen for risk group (iv) is to give general advice together with the laboratory results to those patients having a total cholesterol level of 5.0–6.4 mmol/l, without any further follow-up. To patients with cholesterol levels in the range of 6.5–7.9 mmol/l and LDL levels >5.0, mmol/l or an LDL/HDL ratio >5.0, only non-pharmacological treatment is offered.

Drug treatment of cardiovascular diseases may include the use of calcium channel blockers to expand the arteries so that blood can flow more freely, and anticoagulants to prevent blood clots from forming in diseased arteries. Some studies indicate that compounds such as acetylsalicylic acid and sulphinpyrazone, which may reduce and/or inhibit clotting by reducing platelet reactivity, may also prevent formation of a thrombus. In advanced cases, surgery to replace diseased blood vessels with grafts of healthy arteries may be necessary.

Also, various lipid-lowering drugs have been advocated, as some studies have shown or indicated that even for otherwise healthy patients suffering from mild or moderate hypercholesterolemia, coronary morbidity and mortality is reduced when they are treated with such lipid-lowering drugs. The most widely used lipid-lowering drugs in recent years have been statins, such as HMG-CoA-reductase-inhibitors, bile acid resins, fibrates, nicotinic acid derivatives and various fish oil concentrates with a high content of ω-3-fatty acids.

An increased serum level of triglycerides is now regarded as a risk factor for the development of a cardiovascular disease. importantly, recent studies have indicated that serum levels of triglycerides currently considered as "normal"–200 mg per deciliter of serum may in fact be too high. It has been proposed that the "normal" limit for triglycerides should be reduced by as much as 50 percent as compared to the limit presently regarded as being the "normal" limit (Yahoo News, May 1, 1998). In a group of patients examined over almost 20 years, a serum triglyceride level of more than 100 mg per deciliter serum actually increased the relative risk of contracting a new cardiovascular event by 50 percent and reduced the chance of surviving that event. It was emphasized that so far no clinical trials have examined whether lowering triglyceride levels affects the incidence of subsequent cardiovascular events, and research into the effect of serum triglyceride levels on cardiovascular events lags far behind research directed to establishing the effect of increased cholesterol serum levels on the subsequent development of cardiovascular diseases.

Adlercreutz (Finnish Medical Society, Ann. Med. 29, 95–120 (1997)) has reviewed the phytoestrogen classes of lignans and isoflavones and has described their influences on a range of cellular activities and metabolic events. Soy intake is reported to prevent oxidation of LDL, but no antioxidant mechanism has yet been established. Although isoflavonoids may prevent the development of atherosclerosis, it is a problem to separate the phytoestrogen effect from the effect of other components in foods. It is emphasized that phytoestrogens, particularly in association with soy intake, seem to have a great potential for preventing cardiovascular diseases, but as the area is really in the early stages of development, an established beneficial effect of soy and isoflavonoids in this respect will have to await further studies. It is further stated that despite an abundant literature at this early stage of dietary phytoestrogen research, much work is needed before any recommendation as to phytoestrogen consumption can be made. However, experimental and epidemiological evidence does support the view that these compounds do not have any negative effects and that they may form a group of substances with a great potential in preventive medicine. It is emphasized that at present, no definite recommendations can be made as to the dietary amounts needed for disease prevention. No reference is made to a composition comprising a combination of soy protein, a high content of a phytoestrogen compound, and dietary fibres.

Anderson (N. Eng. J. Med. 333, 276–282 (1995)) analysed a total of 38 clinical trials and concluded that the consumption of soy protein significantly decreases serum levels of total cholesterol, LDL-cholesterol and triglycerides. It was found that ingestion of diets containing soy protein, as compared with control diets, was accompanied by a significant reduction in serum concentrations of total cholesterol, LDL-cholesterol and triglycerides. However, soy protein intake did not significantly affect serum HDL-cholesterol concentrations. The effect of soy protein intake was dependent upon initial cholesterol concentration. Subjects with normal cholesterol levels had non-significant reductions of 3.3 percent, and also subjects with mild hypercholesterolemia had non-significant reductions of 4.4 percent. Only subjects with moderate and severe hypercholesterolemia had significant decreases in cholesterol levels of 7.4 percent and 19.6 percent, respectively. The pattern of changes in serum LDL-cholesterol concentrations was similar to the pattern for total cholesterol concentrations. Also changes in serum triglyceride concentrations were significantly related to the initial serum triglyceride concentrations. Various types of soy proteins were studied, such as isolated soy protein, textured soy protein, or a combination thereof, and it was found that the type of soy protein did not have any significant effect on the net change in serum cholesterol levels. The study did not consider a simultaneous intake of the various types of soy proteins along with dietary fibres. No reference is made to a composition comprising a combination of soy protein, a high content of a phytoestrogen compound, and dietary fibres.

Bakhit (J. Nutr. 124, 213–222 (1993)) studied mildly hypercholesterolemic men receiving a baseline diet and reported that adding of 25 g of soybean protein to a low-fat, low-cholesterol diet lowers total cholesterol concentrations in men with elevated blood lipids. In subjects having lower blood cholesterol concentrations (<5.7 mmol/l), this level of soybean protein intake did not influence blood lipids, and it was suggested that plasma lipids may even be elevated in some subjects following soybean ingestion. Also, other studies have found that in general, individuals with preexisting hypercholesterolemia respond to soybean protein, whereas individuals with normal cholesterol values do not. Bakhit et al. did not observe an additive effect of concurrent ingestion of soybean protein and soybean fibre. No reference is made to a composition comprising a combination of soy protein, a high content of a phytoestrogen compound, and dietary fibres.

Faggiotto (Atherosclerosis Reviews 21, 187–194 (1990)) states that atherosclerosis is an extremely complex disease involving different pathological processes such as inflammation and degeneration. The onset of atherosclerosis and its progression are very subtle, slow and silent processes, often overlapping with a normal ageing process. It is stressed that despite a tremendous quantity of accumulated information, it is not possible to fully explain why atherosclerosis is so common in Western civilization, how fatty streaks develop in young people, how fatty streaks are converted into fibrous plaques, and what the role is of inflammation in e.g. atherosclerosis. It is stated that even when atherosclerosis becomes symptomatic, the treatment of choice often resorts to surgical procedures, as medical intervention has little or no short-term usefulness, unless patients are subjected to a relatively long-term and aggressive therapy. No reference is made to a composition comprising a combination of soy protein, a high content of a phytoestrogen compound, and dietary fibres.

Gooderham (J. Nutr. 126(8), 2000–2006 (1996)) has suggested that although soy protein supplementation to a typical Western diet may indeed increase plasma concentrations of isoflavones, this may not necessarily be sufficient to counter heart disease risk factors such as high serum levels of cholesterol and triglycerides, and platelet aggregation. Any increase in serum levels of isoflavones following intake of a soy rich diet was found to be quite variable among analysed subjects. This was thought to be due to e.g. the timing of the soy protein consumption or the composition of the gut flora. The metabolism of isoflavones in the gut is variable among individuals and remains to be elucidated. It is noted that the levels of isoflavones present in human plasma are most likely not sufficient to mediate a significant inhibition of platelet aggregation. It is stressed that the isoflavones in human plasma predominantly exist in the inactive glucuronide conjugated form, and only a small amount such as approx. 10 percent exists in the active free and sulphate conjugated forms. A lack of an effect of isoflavones on total cholesterol levels in one study was reported to be in agreement with others which also found that soy had little effect in normocholesterolemic individuals, whereas hypercholesterolemic subjects generally exhibited a decreased total and LDL-cholesterol level relative to normocholesterolemic subjects. It was stressed that only a few studies have reported an HDL-cholesterol raising effect due to the consumption of soy protein and that most studies have shown little or no effect on HDL-cholesterol levels. The reported results indicate a similar lack of effect of soy protein on HDL-cholesterol levels in normocholesterolemic subjects. It is emphasized that only recently have isoflavones been examined separately to determine if these compounds are responsible for the lipid lowering effects associated with intake of soy proteins. the administration of purified isoflavones to animals has shown variable results on blood lipids. One study conducted on hypercholesterolemic humans failed to show an effect of purified isoflavones on blood lipid levels. No reference is made to a composition comprising a combination of soy protein, a high content of a phytoestrogen compound, and dietary fibres.

Hendrich (J. Nutr. 1(9 Suppl.), 1789S–1792S (1994)) has reported that isoflavones may be of great potential benefit to human health maintenance and that isoflavones may be health-protective in amounts potentially available from a human diet containing daily soy foods. The food content of isoflavones is in the range of from 0.1 to 1 mg/g in soy foods. Several factors such as variety of soybean, processing and the addition of other ingredients to the food influence isoflavone contents of foods. It is stated that human intestinal bacteria can destroy ingested isoflavones to a great extent and that this may be why only 15 to 20 percent of isoflavones are reported to be recoverable in intact form from the urine and faeces. It is emphasized that much work remains to, determine the relation between concentration of isoflavones in human urine and plasma and the biological effects of the isoflavones. It is noted that although more health-related animal data need to be obtained, the time is approaching when, long-term human feeding trials of purified isoflavones and foods containing isoflavones to examine health-related outcomes may be warranted. No reference is made to a composition comprising a combination of soy protein, a high content of a phytoestrogen compound, and dietary fibres.

Hunninghake (Am J. Med. 97, 504–508 (1994)) discloses an evaluation of hypocholesterolemic effects of a long-term treatment with a mixture of dietary fibres administered twice a day. 59 subjects with moderate hypercholesterolemia who completed the 15-week placebo-controlled study with the dietary fibre were treated for an additional 36 weeks with 20 g/day of fibre. There were no significant effects on the levels of either triglycerides or HDL. Levels of total cholesterol and LDL-cholesterol and the HDL/LDL-ratio were significantly reduced during treatment. The mean percentage reductions from baseline after 51 weeks of treatment were approximately 5 percent for total cholesterol, 9 percent for LDL-cholesterol, and 11 percent for the LDL/HDL ratio. No reference is made to a composition comprising a combination of soy protein, a high content of a phytoestrogen compound, and dietary fibres.

Knight (Maturitas 22, 167–175 (1995)) provides a synopsis of the literature relating principally to the clinical effects of phytoestrogens on the diseases associated with ageing. A review of literature pertaining to cardiovascular diseases states that the protective effects of phytoestrogens are manifested through lipid changes, a decrease in LDL-cholesterol and an increase in HDL-cholesterol, and vascular effects, concerning both vasomotor tone and vessel wall compliance. The consumption of soy protein is reported to alter lipid levels and dietary soy protein appears to be anti-atherogenic when compared with various animal proteins. It is concluded that isoflavones represent a large and exciting group of compounds with potential benefits to many diseases. It is emphasized that current evidence justifies the conclusion that phytoestrogens may be among the dietary factors affording protective effects against heart disease. However, further clinical studies are required to more clearly elucidate their effects. No reference is made to a composition comprising a combination of soy protein, a high content of a phytoestrogen compound, and dietary fibres.

Knight (Obstet. Gynecol. 87, 897–904 (1996)) has reviewed the sources, metabolism, potencies, and clinical effects of phytoestrogens on humans. The review suggests that phytoestrogens are among the dietary factors affording protection against heart disease in vegetarians. Based on epidemiologic and cell line studies, it is emphasized that intervention studies are now an appropriate consideration to assess the clinical effects of phytoestrogens because of the potentially important health benefits associated with the consumption of foods containing these compounds. It is concluded that clinical applications for phytoestrogens are still in their infancy. No reference is made to a composition comprising a combination of soy protein, a high content of a phytoestrogen compound, and dietary fibres.

Packard (Arterioscler. Thromb. Vasc. Biol. 17, 3542–3556 (1997)) has reviewed the heterogeneity in the apoB containing lipoprotein classes and provides an interpretation of kinetic studies of apoB metabolism in the light of underlying structural and functional variations. The review is based on the fact that lipoprotein classes are composed of a limited number of components with distinct properties. However, the basis for this heterogeneity and the consequences for disease are not thoroughly understood. The LDL-fraction is made up of a small number of subtypes of particles with relatively discrete size and density. Subjects with a preponderance of small-sized LDL have a three-fold increased risk of having a myocardial infarction independent of the total concentration of LDL present. No reference is made to a composition comprising a combination of soy protein, a high content of a phytoestrogen compound, and dietary fibres.

Potter (Am. J. Clin. Nutr. 5, 501–506 (1993)) studied the effects of soy protein consumption with and without soy fibre on plasma lipids in mildly hypercholesterolemic men. It was reported that total and LDL-cholesterol concentrations can be lowered significantly in mildly hypercholesterolemic men, as indicated by a replacement of 50 percent of dietary protein with soy protein. Similar reductions in blood lipids were noted for isolated soy protein, whether it was consumed in conjunction with soy cotyledon fibre or cellulose fibre. Plasma triglyceride concentrations were unaffected by the various dietary treatments described in the article. The study did not reveal any additive cholesterol-lowering effect of concurrent intake of cotyledon soy fibre with isolated soy protein, and it was stated that whether or not there is an added benefit in lowering blood cholesterol concentrations from increased concurrent intake of soy protein and fibre in humans is not known. No reference is made to a composition comprising a combination of soy protein, a high content of a phytoestrogen compound, and dietary fibres.

Reinli (Nutr. Cancer 26, 123–148 (1996)) has reviewed the literature for quantitative data on the levels of known phytoestrogens (daidzein, genistein, coumestrol, formononetin and biochanin A) in food plants. It is reported that the isoflavones daidzein and genistein may exist in four related chemical structures, i.e. an aglycone structure (daidzein and genistein), a 7-O-glucoside structure (daidzin and genistin), a 6'-O-acetylglucoside structure (6'-O-acetyldaidzin and 6'-O-acetylgenistin), and a 6'-O-malonylglucoside structure (6'-O-malonyldaidzin and 6'-O-malonylgenistin). The conjugates (7-O-glucosides, 6'-O-acetylglucosides, and 6'-O-malonylglucosides) are transformed to aglycones, which are sometimes called free isoflavones, through hydrolysis in the intestinal tract by β-glucosidase enzymes of gut bacteria. Acid hydrolysis in the stomach may also contribute to the formation of free isoflavones. It is unclear how readily conjugates undergo intestinal hydrolysis and subsequent absorption. It is stressed that isoflavones are metabolised differently by different animals and humans. No reference is made to a composition comprising a combination of soy protein, a high content of a phytoestrogen compound, and dietary fibres.

Sniderman (Am J. Cardiol. 79, 64–67 (1997)) presents a risk factor hypothesis with an emphasis on the integral role of LDL in atherogenesis. It is stressed that a measurement of LDL-cholesterol is an incomplete estimate of the risk attributable to LDL and that other classic risk factors such as e.g. hypertension, diabetes, and smoking exert their proatherogenic potential largely or exclusively by multiplying the malign influences of LDL on the arterial wall. It is acknowledged that small, dense LDL-particles are one of the most common dyslipoproteinemias associated with coronary artery disease. It is reported that elevated levels of lipoprotein (a) are associated with increased coronary risk, but the basis for this is still not clear. No reference is made to a composition comprising a combination of soy protein, a high content of a phytoestrogen compound, and dietary fibres.

WO 95/10512 relates to a process for producing an aglucone isoflavone enriched vegetable protein whey and discloses in one embodiment a whey having a dry basis genistein content of about 2.6 to about 8.7 mg/gram and a dry basis daidzein content of about 2.5 to about 6.0 mg/gram. No reference is made to a composition comprising a combination of soy protein, a high content of a phytoestrogen compound, and dietary fibres.

WO 95/1b529 relates to a process for producing an aglucone isoflavone enriched protein concentrate and discloses in one embodiment a concentrate having on a dry basis a genistein content of about 1.0 to about 2.0 mg/gram and a daidzein content of about 0.7 to about 1.5 mg/gram. No reference is made to a composition comprising a combination of soy protein, a high content of a phytoestrogen compound, and dietary fibres.

WO 95/10530 relates to a process for producing an aqueous extract comprising protein and glucone isoflavones and discloses in one embodiment a vegetable protein isolate having a dry basis genistein content of about 1.5 to about 3.5 mg/gram and a dry basis daidzein content of about 1.0 to about 3.0 mg/gram. No reference is made to a composition comprising a combination of soy protein, a high content of a phytoestrogen compound, and dietary fibres.

WO 97/31546 discloses data from total replacement programmes (for 6 weeks) in weight reduction studies conducted at Karolinska Hospital in Sweden. It is shown that products comprising isolated soy protein and soybean cotyledon fibres reduce serum triglyceride levels by a maximum of 44 percent and cholesterol levels by a maximum of 27 percent for a patient population with a mean initial cholesterol content of 5.6 mmol/l. A mean value of 6.25 mmol/l was determined for all patients having serum cholesterol levels above 6 mmol/l, and for this group of patients a reduction in serum cholesterol levels of 33 percent was observed. Since the reported data were part of a weight reduction programme, a dietary effect and/or an effect related to a weight loss would have contributed to the observed reductions in cholesterol and/or triglycerides. No reference is made to a composition comprising a combination of soy protein, a high content of a phytoestrogen compound, and dietary fibres.

WO 97/37547 discloses an isoflavone-enriched soy protein product having a protein content greater than 60 percent of total dry matter, a total dietary fibre content of less than 4 percent of total dry matter, a sucrose content greater than 10 percent of total dry matter, a total content of sulphur-containing amino acids greater than 2.2 percent of the total amino acid content, a stachyose content of less than 1.5 percent of total dry matter, and a total isoflavone content greater than 2.5 mg/gram, equivalent to 0.25 percent. The use of soy cotyledon fibres is not anticipated and the claimed invention is for use as an ingredient in the production of an edible product and not in a treatment of arteriosclerosis. Also, the product differs from the composition according to the present invention by comprising total dietary fibre in an amount of less than 4 percent of total dry matter, by containing an unusually low amount of stachyose and a high amount of sulphur-containing amino acids.

U.S. Pat. No. 5,320,949 discloses a process for producing an aglucone isoflavone enriched fibre product from a vegetable protein material in the form of a slurry and discloses in one embodiment an aglucone enriched fibre product directly obtainable from said process and having a genistein content of about 1.0 and 2.0 mg/gram and a daidzein content of about 0.7 to 1.7 mg/gram. No reference is made to a composition comprising a combination of soy protein, a high content of a phytoestrogen compound, and dietary fibres. No reference is made to a composition comprising soy cotyledon fibres and a phytoestrogen compound.

U.S. Pat. No. 5,352,384 discloses an aglucone enriched fibre product having a genistein content of about 1.0 to 2.0 mg/gram and a daidzein content of about 0.7 to 1.7 mg/gram. No reference is made to a composition comprising a combination of soy protein, a high content of a phytoestrogen compound, and dietary fibres.

EP 827 698 A2 and EP 827 698 A3 disclose a process for producing an aglucone isoflavone enriched extract from a vegetable material containing isoflavone conjugates and protein. No reference is made to a composition comprising a combination of soy protein, a high content of a phytoestrogen compound, and dietary fibres.

An abstract presented at the American Heart Association's 38$^{th}$ Annual Conference on Cardiovascular Disease Epidemiology and Prevention held in March 1998 disclosed a reduction in the levels of total and LDL-cholesterol in a subject following intake of a diet supplemented with 25 grams of soy protein containing 4 mg, 25 mg, 42 mg, and 58 mg of isoflavones, respectively. A "dose-response" effect was reported so that increasing amounts of isoflavones were associated with an increasing reduction of cholesterol. A maximum reduction of serum levels of total and LDL-cholesterol of 4 percent and 7 percent, respectively, was reported for the product containing 58 mg of isoflavone. No reference is made to a composition comprising a combination of soy protein, a high content of a phytoestrogen compound, and dietary fibres.

SUMMARY OF THE INVENTION

The present invention provides a nutritional composition having a high, fixed amount of a phytoestrogen compound such as e.g. naturally occurring isoflavones. More particularly the present invention provides a nutritional composition of soybean extractable ingredients having a high, fixed amount of a phytoestrogen compound such as e.g. naturally occurring isoflavones.

More particularly, the present invention relates to a combination comprising a) soy protein, preferably isolated soy protein, b) a high content of a plant hormone in the form of a phytoestrogen compound, preferably naturally occurring isoflavones, and c) dietary fibres, preferably soybean fibres, more preferably soybean fibres manufactured from the cotyledon of soybeans hereinafter referred to as soy cotyledon fibres.

The present invention is useful in treating including prophylactically treating cardiovascular diseases such as hypercholesterolemia, hypertriglyceridemia, hyperlipidemia and other cardiovascular diseases such as e.g. arteriosclerosis. It is one objective of the present invention to significantly reduce levels of total serum cholesterol and LDL-cholesterol and triglycerides in a mildly hypercholesterolemic subject. It is another objective of the present invention to significantly reduce levels of total serum cholesterol and LDL-cholesterol and triglycerides in a subject suffering from hypercholesterolemia and/or hyperlipidemia. It is another objective of the present invention to render the arterial wall more resistant to the accumulation of lipoproteins. It is a further objective of the present invention to provide a composition effective in treating and/or prophylactically treating and/or preventing and/or alleviating an arteriosclerotic condition by reducing the influx of cholesterol and/or triglycerides into the endocelium of the arterial wall. Yet another objective of the present invention is to reduce lipid plaque formation. A composition according to the present invention may be comprised in a micronutrient as defined herein below.

Phytoestrogen compounds are naturally occurring plant hormones showing a structural similarity to 17β-estradiol. Phytoestrogens consist of a number of classes including isoflavones, coumestans, lignans and resorcylic acid lactones. The class of isoflavones consists of among others genistein, daidzein, equol, glycitein, biochanin A, formononetin, and O-desmethylangolesin. The isoflavones genistein and daidzein are found almost uniquely in soybeans. When present in the plant the isoflavones are mainly in a glucoside form, i.e. attached to a sugar molecule. Isoflavones in this glucoside form can be deconjugated to yield isoflavones in a so-called aglycone form, which is the biologically more active form of isoflavones and which is absorbed faster and to a greater extent in the human gut than isoflavones in the glucoside form. In vitro studies have examined the relative estrogenic effect exerted by various phytoestrogens including isoflavones. The resulting potencies as compared to estradiol (having a relative potency of 100), have been reported by Knight (Maturitas 22, 167–175 (1995)) for among others genistein (0.084) and daidzein (0.013).

However, the results also showed that the estrogen receptor complexes formed by estradiol and isoflavones such as genistain and daidzein are functionally equivalent, The comparative dissociation constant of genistein for the estrogen receptor, as determined In competitive binding assays, was found to be from 100 to 10,000 times higher than that of estradiol.

The term "naturally occurring" substance as used in the present specification and the appended claims refers to a substance originally isolated from a natural source, such as an animal or a plant, for example a soy plant, or modified forms of such a substance. The naturally occurring substance for use in a composition according to the present invention may be Included in a composition according to the present invention as part of the natural source or in any type of extract, isolate or the like thereof, or it may have been isolated from a plant source or synthesized biologically, microbiologically, or chemically or by any other means.

Soy proteins are involved in a reduction of cholesterol and triglyceride levels, they are easily digestible, and they represent an efficient sole protein source for maintaining the nitrogen balance. Soy isoflavones in high intakes further enhances this effect, Dietary fibres, such as soybean fibres, especially soy cotyledon fibres have been shown to reduce total serum cholesterol levels, to normalise the gastrointestinal function, and to exert no influence on the absorption of essential minerals.

Accordingly, in one aspect the present invention provides a composition comprising
  (a) a soy protein source, selected from isolated soy protein, soy protein concentrate, or soy flour, said soy protein source providing an amount of soy protein, which is at least 45 weight percent of the total protein content of the composition, said total protein content providing at least 15 percent of the total energy content of the composition,
  (b) at least one phytoestrogen compound in an amount of more than 0.16 weight percent of the soy protein content of the composition, and
  (c) dietary fibres in an amount of more than 6 weight percent of the total weight of the composition on a dry basis.

In a more preferred aspect the present invention provides a composition comprising
  (a) isolated soy protein in an amount of at least 50 weight percent of the total protein content of the composition, said total protein content providing at least percent of the total energy content of the composition,
  (b) at least one phytoestrogen compound in an amount of more than 0.16 weight percent of the soy protein content of the composition, and
  (c) soybean fibres in an amount of more than 6 weight percent of the total weight of the composition on a dry basis.

In a most preferred aspect the present invention provides a composition comprising
  (a) isolated soy protein in an amount of at least 50 weight percent of the total protein content of the composition, said total protein content providing at least percent of the total energy content of the composition,
  (b) at least one phytoestrogen compound in an amount of more than 0.16 weight percent of the say protein content of the composition, and
  (c) soy cotyledon fibres in an amount of more than 6 weight percent of the total weight of the composition on a dry basis.

Phytoestrogen compounds are naturally occurring plant substances, which are either structurally or functionally similar to 17β-estradiol or generate estrogenic effects. Phytoestrogens consist of a number of classes including isoflavones, coumestans, lignans and resorcylic acid lactones. Examples of isoflavones according to the present invention are genistein, daidzein, equal, glycitein, blochanin A, formononetin, and O-desmethylangolesin. The phytoestrogen compounds of a composition according to the present invention are, preferably isoflavones, more preferably genistein, daidzein, glycitein and/or equol, yet more preferably genistein and/or daidzein and even more preferably genistein. Genistein and daidzein are found almost uniquely in soybeans. A preferred composition according to the present invention may accordingly comprise a single isoflavone, such as genistein, daidzein, glycitein or equol, or it may comprise at least one isoflavone selected from the group consisting of at least genistein, daidzein, glycitein and equol.

A composition according to the present invention may be capable of preventing and/or alleviating and/or treating and/or prophylactically treating an arteriosclerotic condition by reducing the accumulation of cholesterol in the arterial wall. This inhibitory effect may be mediated by the binding of naturally occurring isoflavones and/or soy peptides to an estrogen receptor or estrogen-like receptor present in the endocelium of an artery. The soy peptides are preferably provided by partial hydrolysis of soy protein.

Both plasma cholesterol and triglyceride levels are usually increased in individuals treated for a cardiovascular disease, and these increased levels, unless reduced by treatment, are likely to promote atherosclerosis and/or coronary heart disease (CHD). Beta-2-receptors are present on many different types of cells including fat cells and cells of the arterial wall. Beta-2-adrenergic receptors are involved in the regulation of triglyceride synthesis in fat cells and according to one presently preferred hypothesis, binding of soy peptides and/or a phytoestrogen compound such as e.g. a naturally occurring isoflavone to a beta-2-receptor present on a fat cell or in an arterial wall is effective in reducing e.g. the synthesis of triglycerides in fat cells and/or the release of triglycerides into the blood stream and/or reducing the influx of cholesterol and/or triglycerides into the arterial wall. The soy peptides are preferably provided by partial hydrolysis of soy protein.

According to a preferred hypothesis, a composition according to the present invention will reduce and/or eliminate one or more of the risk factors for cardiovascular diseases. Accordingly, a composition according to the present invention may be effective in preventing and/or prophylactically treating and/or alleviating and/or treating conditions such as e.g. hypercholesterolemia, hypertriglyceridemia, hypertension and hyperglycemia. A composition according to the present invention may also be capable of reducing, preventing and/or eliminating fatty streak formation and/or fibrous plaque development and/or effective in mediating a regression of one or both of said arteriosclerotic conditions.

According to a preferred hypothesis, a composition according to the present invention will lead to a decrease in total serum cholesterol levels and/or a decrease in serum LDL-cholesterol levels and/or a decrease in serum triglyceride levels and/or effectively increase the HDL/LDL-cholesterol ratio and/or effectively increase serum levels of high-density lipoproteins (HDL) and/or generate a decrease in serum levels of low-density lipoproteins (LDL). It is desirable to achieve an elevated HDL/LDL-cholesterol ratio since this may result in an increased reverse cholesterol transport and a subsequent excretion.

Also, it is believed that a composition according to the present invention will affect ApoB lipoprotein metabolism including the metabolism of a recently discovered class of ApoB comprising lipoprotein particles called small, dense LDL-particles. The LDL-class of lipoproteins is in fact composed of several components with distinct properties. The basis for this heterogeneity and the consequences for disease are at present not thoroughly understood. An increased level of small, dense LDL-particles is one of the most common dyslipoproteinemias associated with coronary artery disease, and serum levels of ApoB are often disproportionately elevated compared with LDL-cholesterol in dyslipoproteinemic patients.

Heterogeneity within lipoprotein classes may be the result of a differing lipid content, a different apoprotein composition, an altered protein conformation or an as yet unidentified structural variation. Subjects with a preponderance of small, dense LDL have an increased risk of suffering a myocardial infarction independent of the total concentration of serum LDL. Accordingly, a composition according to the present invention may be effective in lowering elevated levels of small, dense LDL.

Hypertriglyceridemia is associated with an increase in the clotting activities of thrombogenic factors such as e.g. factor VII and/or factor X and/or factor XII and an increase in the level of the inhibitor of tissue plasminogen activator, PAI-1. The increased inhibitor concentration results in a decreased level of plasminogen synthesis and thus a decreased level of plasminogen stimulated clot lysis. These changes in clotting activities contribute to a procoagulant state. According to one presently preferred hypothesis the present invention also provides a composition effective in normalising levels of homocystein and/or the clotting activities of at least one thrombogenic factor such as e.g. factor VII and/or factor X and/or factor XII by e.g. decreasing the increased activity thereof. Also, a composition according to the present invention may be effective in promoting a decrease in the level of the inhibitor of tissue plasminogen activator, PAI-1, which in turn leads to an increased plasminogen stimulated clot lysis. A composition according to the present invention may also be effective in reducing an increased platelet aggregatability and/or mediating directly or indirectly a reduction in the increased level of lipoprotein (a) associated with a procoagulant state in an arteriosclerotic condition.

Accordingly, in one embodiment the present invention provides a composition effective in reducing and/or eliminating risk factors for coronary heart disease (CHD) in obese subjects. Consequently, a composition according to the present invention may be capable of preventing and/or alleviating and/or treating and/or prophylactically treating and/or eliminating hypertriglyceridemia and/or hypercholesterolemia and/or hyperglycemia and/or hypertension and/or effective in mediating an increased HDL-LDL-cholesterol ratio.

A composition according to the present invention may also be effective in treating dyslipidemia such as e.g. hypertriglyceridemia and/or hypercholesterolemia in connection with increased VLDL, decreased and altered HDL and small dense LDL, and hypertension, all of which are risk factors for atherosclerosis. Accordingly, in one embodiment, a composition according to the present invention may be capable of effectively decreasing and/or eliminating increased serum levels of VLDL, and/or effectively increasing decreased serum levels of HDL, and/or effectively decreasing serum LDL levels including serum levels of small dense LDL. A composition according to the present invention may be capable of preventing and/or treating and/or prophylactically treating and/or alleviating hypertension.

A composition according to the present invention may also be effective in suppressing any effect that would otherwise generate an increased turnover of arterial smooth muscle cells and/or lead to an increased cholesterol ester accumulation in the arterial wall.

In hypercholesterolemia characterised by increased levels of intracellular cholesterol resulting from e.g. increased delivery of LDL-cholesterol via the LDL-receptor, a composition according to the present invention may be effective in reducing the increased activity of the LDL-receptor. A composition according to the present invention may also be capable of alleviating, eliminating and/or treating any decrease in the HDL receptor-mediated cholesterol efflux. Accordingly, a composition according to the invention may be capable of reducing and/or eliminating any enhanced retention of intracellular cholesterol caused by a decreasing HDL receptor-mediated cholesterol efflux.

Modifications of lipoproteins constitute another risk factor for cardiovascular disease. The modification characterised by protein glycosylation is associated with e.g. arteriosclerosis, and glycosylated lipoproteins such as e.g. LDL, IDL, VLDL and HDL can be expected to be functionally abnormal. Accordingly, the accumulation of glycosylated LDL in the plasma can be perceived to enhance cholesterol ester accumulation. Also, glycosylation of HDL can be expected to impair the ability of HDL binding to the HDL receptor. This impaired binding is likely to reduce the level of intracellular cholesterol efflux. Accordingly, glycosylated HDL may well be another factor potentially contributing to the accumulation of cholesterol in the arterial cell wall. A composition according to the present invention may be effective in preventing, alleviating, treating, reducing and/or eliminating lipoprotein glycosylation in the serum of subjects. In addition, a composition according to the present invention may also be effective in preventing lipoprotein modification caused e.g. by oxidation, chemical modification such as chemical cross-linking, or modifications caused by an alteration in the lipid composition of the lipoprotein, such as any increase or decrease in the content of triglycerides, cholesterol esters, free cholesterol, and apolipoproteins.

Glycosylated lipoproteins have been suggested to be the subject of further processing leading to the formation of hyperglycosylated compounds. Glycosylation and hyperglycosylation of proteins including lipoproteins in both plasma and the arterial wall can also be expected to be a risk factor for cardiovascular disease including arteriosclerosis. Accordingly, a composition according to the present invention may be capable of preventing, treating, reducing, alleviating and/or eliminating the accumulation of hyperglycosylated proteins in both serum and cells of the arterial wall. By doing so, the composition is acting to decrease the amount of LDL becoming "trapped" in the arterial wall due to the high degree of glycosylation of arterial wall proteins. A composition according to the present invention may also be effective in alleviating and/or preventing endothelial cell wall alterations generating an increased LDL "trapping", and it may be effective in restoring the formation of cells with normal permeability and adhesion parameters.

Lipoprotein glycosylation, hyperglycosylation, oxidation and/or auto-oxidative glycosylation, are risk factors for cardiovascular disease such as arteriosclerosis.

Accordingly, a composition according to the present invention may be effective in eliminating, preventing, alleviating, treating and/or reducing any incidence of lipoprotein glycosylation, hyperglycosylation, oxidation and/or auto-oxidative glycosylation. According to one presently preferred hypothesis, the phytoestrogen compound of a composition according to the present invention is capable of counteracting such incidences. The phytoestrogen compound may also be capable of preventing, reducing and/or eliminating the formation of e.g. free radicals that are likely to be involved in such processes, and a composition according to the present invention may be effective in being, promoting, and/or facilitating the formation of an effective antioxidant defence system for counteracting glycosylation, hyperglycosylation, oxidation and/or auto-oxidative glycosylation of serum proteins and proteins including lipoproteins of the arterial cell wall.

A composition according to the present invention may be effectively acting as an antioxidant in preventing lipoprotein oxidation and/or glycosylation. By the term auto-oxidative glycosylation, or glycoxidation, is understood a reaction leading to an oxidative modification and/or cross-linking of proteins. An increased production of free radicals and lipid peroxidation may also contribute to the formation of auto-oxidative glycosylated lipoproteins and this contribution may also be effectively prevented and/or eliminated by a composition according to the present invention.

According to another presently preferred hypothesis, the binding of a phytoestrogen compound such as e.g. an isoflavone, optionally in combination with soy peptides preferably provided by hydrolysis of soy protein, to a receptor in the arterial wall, such as e.g. the estrogen receptor, or an estrogen-like receptor, is involved in or effective in controlling accumulation of lipoproteins in the arterial wall, possibly by regulating the permeability of said wall and/or the mechanism of lipoprotein transport across cellular membranes. Consequently, the binding of isoflavones such as e.g. genistein and/or daidzein to a receptor in the arterial wall may reduce the flux of lipoproteins into the arterial wall. Receptor binding of isoflavones in the arterial wall is particularly effective in controlling, preventing and/or eliminating fatty streak formation and/or fibrous plaque development and/or effective in mediating a regression of one or both of said arteriosclerotic conditions.

According to a particularly preferred hypothesis, binding of an isoflavones such as e.g. genistein and/or daidzein to a receptor in the arterial wall, preferably an estrogen receptor or an estrogen-like receptor, results in an increased nitric oxide synthesis in the endothelial cells of the arterial wall. Nitric oxide is known to exert anti-arteriosclerotic effects including inhibition of platelet adhesion and aggregation, and inhibition of smooth muscle cell proliferation. Soy peptides obtainable by hydrolysis of soy protein may participate in the binding of isoflavones to an estrogen receptor or an estrogen-like receptor or the soy peptides may themselves bind to said receptor and exert an action leading to an increased nitric oxide synthesis.

In another presently preferred hypothesis, the establishment of an oxidative potential that promotes lipoprotein oxidation and/or lipoprotein auto-oxidative glycosylation occurs concomitantly with, and is very likely caused by, a decrease in cellular antioxidative defence systems. Accordingly, a composition according to the present invention may be effective in acting as an antioxidant. This action reduces and/or eliminates LDL, VLDL, IDL and/or HDL susceptibility to oxidation.

Furthermore, a composition according to the present invention may also be effective in reducing an enhanced susceptibility to endothelial injury and/or for alleviating and/or restoring and/or improving an inefficient endothelial cell repair mechanism leading to endothelial dysfunction. One effect of such an action exerted by a composition according to the present invention is to direct macrophage development away from foam cell formation and to increase the potential of generating arterial smooth muscle cells.

In another presently preferred hypothesis, a composition according to the present invention will promote and/or mediate a reduction in arterial wall thickness and lead to a reduction in the amount of LDL entering the wall. It is believed that an increased thickness of the arterial wall is positively associated with an increased uptake of LDL-particles that are likely to either aggregate or oxidize within the cells of the arterial wall.

Also, a composition according to the present invention may be capable of reducing, eliminating and/or preventing the formation of increased serum levels of lipoprotein. (a) in a subject. Lipoprotein (a) levels may primarily be genetically determined, and no current cardiovascular medications are thought effective in lowering serum levels of lipoprotein (a).

DETAILED DESCRIPTION OF THE INVENTION

Figure 1:
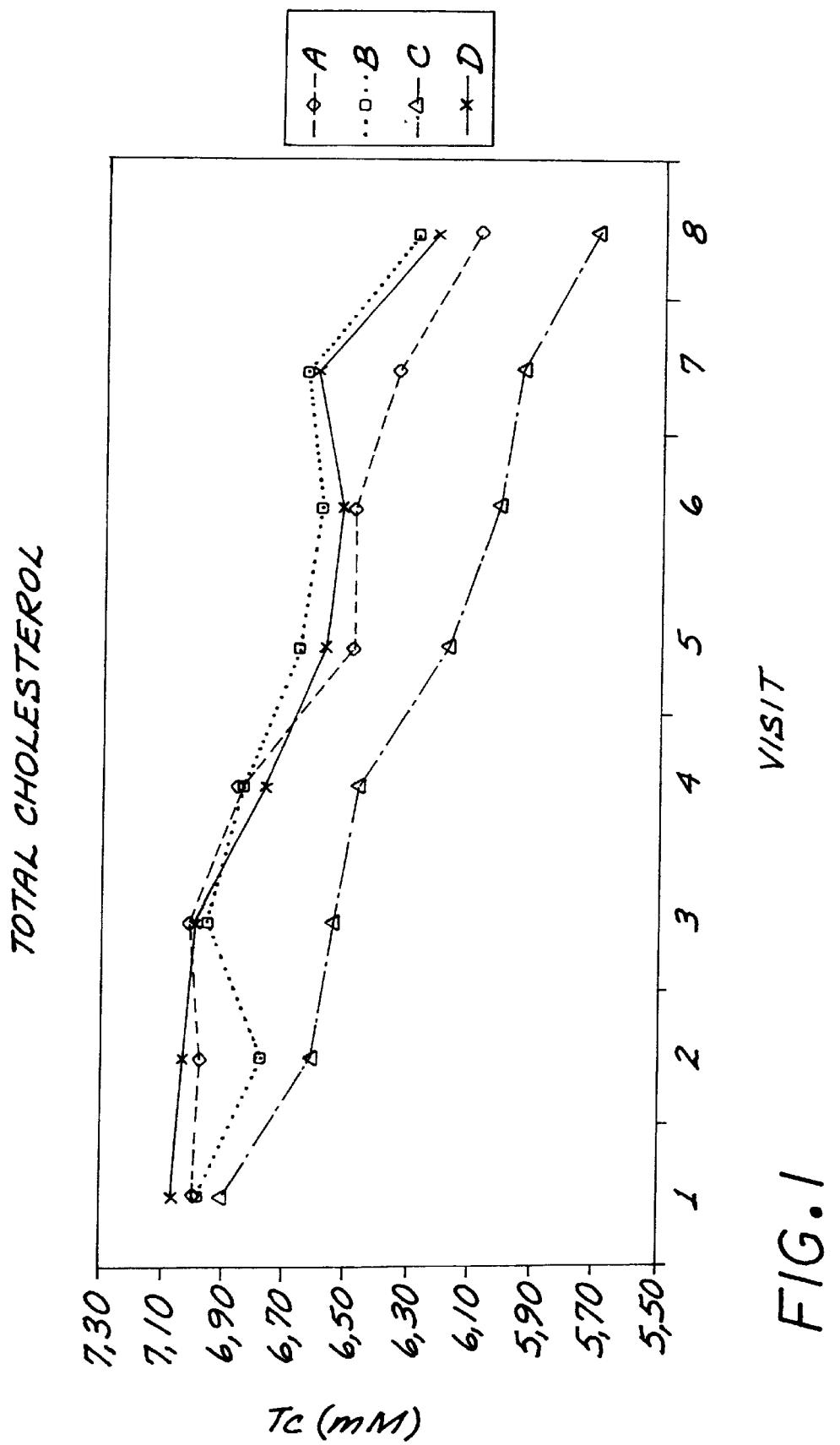
FIG. 1 shows the levels of total cholesterol (mM) for the four groups of patients in Example 2 (A: Patients in Group I; B: Patients receiving placebo with the same intake of protein and fibre as Group I; C: Patients in Group I; D: Patients receiving placebo with the same intake of protein and fibre as Group II) at each of the 8 visits. TC=total cholesterol.

A composition according to the present invention comprises a novel combination of soy protein, preferably isolated soy protein, a phytoestrogen compound, preferably naturally occurring isoflavones, and dietary fibres, preferably soybean fibres, more preferably soy cotyledon fibres.

The soy protein can be provided by isolated soy protein, soy protein concentrate, soy flour or the like or any combination thereof. Isolated soy protein is preferred.

Isolated soy protein is the major proteinacious fraction of soybeans. It is prepared from high quality, dehulled, defatted soybeans by removing a preponderance of the non-protein components resulting in an isolated soy protein fraction which shall contain at least 90 percent protein (N×6.25) on a moisture free basis. The preparation takes place through a series of steps in which the soybean protein portion is separated from the rest of the soybean. The removal of carbohydrate results in a product, which is essentially bland in flavour and therefore particularly useful in a nutritional composition for humans.

Soy protein concentrates are made by removing most of the oil and water-soluble non-protein constituents from defatted and dehulled soybeans. In the present context a soy protein concentrate shall preferably contain at least 65 percent protein on a moisture-free basis.

The soy protein can also be provided by soy flour, which can be full-fat or defatted soy flour. Full-fat soy flour comes from whole, dehulled soybeans that have been ground into a fine powder and. as the name implies, still contains the fat naturally found in soybeans. Defatted soy flour comes from whole, dehulled, defatted soybeans that have been ground into a fine powder. Soy flour is approximately 50 percent soy protein on a dry weight basis in the present context.

The soy protein used in a composition according to the present invention should preferably supply all the essential amino acids in the amounts required for humans. Preferably, the soy protein should also meet or exceed the essential amino acid requirement pattern for children and adults as established by the Food and Agricultural Organisation, World Health Organisation and United Nations University (FAO/WHO, UNU). Furthermore, the preferred soy protein should be comparable in digestibility to milk, meat, fish, and egg protein. Finally, the preferred soy protein shall be effective in maintaining nitrogen balance when consumed at the recommended protein intake level.

Preferred isolated soy protein products meeting the foregoing requirements are supplied by Protein Technologies International, Inc. under the brand name SUPRO®. SUPRO® isolated soy proteins are supplied in many different qualities and SUPRO® XT 12C is one particularly preferred quality. The currently most preferred quality is termed SUPRO® FXP-HO159.

The soy protein is preferably the main or sole protein source in a nutritional composition according to the present invention. However, parts of the protein source may be provided by other proteins such as e.g. skimmed milk, preferably as a powder, and other vegetable or animal proteins including diary proteins. Preferably, at least 45 weight percent, such as 50 weight percent, for example at least 60 weight percent, such as at least 70 weight percent, for example at least 75 weight percent, such as at least 80 weight percent, for example at least 85 weight percent, such as at least 90 weight percent, for example at least 95 weight percent, such as at least 98 weight percent of the total protein content of the composition is soy protein, and more preferably substantially all of the protein is soy protein.

In a preferred embodiment of the invention the soy protein is provided by isolated soy protein. In this embodiment, preferably at least 50 weight percent, for example at least 60 weight percent, such as at least 70 weight percent, for example at least 75 weight percent, such as at least 56 weight percent, for example at least 85 weight percent, such as at least 90 weight percent, for example at least 95 weight percent, such as at least 98 weight percent of the total protein content of the composition is isolated soy protein, and more preferably substantially all of the protein is provided by isolated soy protein.

The total protein content of a composition according to the present invention provides at least 15 percent of the total energy content of the composition, for example 18 percent, such as at least 20 percent, for example at least 22 percent, such as at least 25 percent, for example at least 28 percent, such as at least 30 percent, for example at least 32 percent, such as at least 35 percent, for example at least 38 percent, such as at least 40 percent, for example at least 42 percent, such as at least 45 percent, for example at least 48 percent, such as at least 50 percent of the total energy content of the composition, and preferably less than 90 percent of the total energy content of the composition.

Phytoestrogen compounds according to the present invention are defined as naturally occurring plant substances, said substances being either structurally or functionally similar to 17P-estradiol or generating estrogenic effects. Phytoestrogens consist of a number of classes including isoflavones, coumestans, lignans and resorcylic acid lactones. Examples of isoflavones according to the present invention are genistein, daidzein, equol, glycitein, biochanin A, formononetin, and O-desmethylangolesin. The phytoestrogen compounds of a composition according to the present invention are preferably isoflavones, more preferably genistein, daidzein, glycitein and/or equal, yet more preferably genistein and/or daidzein, and even more preferably genistein. A preferred composition according to the present Invention may accordingly comprise a single isoflavone, such as genistein, daidzein, glycitein or equal, or it may comprise at least one isoflavone selected from the group consisting of at least genistein, daidzein, glycitein and equal. When present in the plant the isoflavones are mainly in a glucoside form, i.e. attached to a sugar molecule. This glucoside form can be deconjugated to yield a so-called aglycone form, which is the biologically active species. A composition according to the present invention may comprise isoflavones in glucoside and/or aglycone forms regardless of whether the deconjugation to the aglycone form has taken place biologically, in vitro or by any other means whereby the isoflavones are included In a composition according to the present invention or if the aglycone forms are the native form of the isoflavones.

The phytoestrogen compound is preferably present in an amount of at least about 0.16 weight percent of the soy protein content, such as at least about 0.1 8 weight percent, for example at least about 0.20 weight percent, such as at least about 0.22 weight percent, for example at least about 0.24 weight percent, such as at least about 0.25 weight percent, for example more than about 0.25 weight percent, such as at least about 0.26 weight percent, for example at least about 0.28 weight percent, such as at least about 0.30 weight percent, for example at least about 0.32 weight percent, such as at least about 0.33 weight percent, for example more than about 0.33 weight percent, such as at least about 0.35 weight percent, for example at least about 0,40 weight percent, such as at least about 0.45 weight percent, for example at least about 0.50 weight percent, such as at least about 0.55 weight percent, for example at least about 0.60 weight percent, such as at least about 0.65 weight percent, for example at least about 0.70 weight percent, such as at least about 0.75 weight percent, for example at least about 0.80 weight percent, such as at least about 0.85 weight percent, for example at least about 0.90 weight percent, such as at least about 1.0 weight percent of the soy protein content, and preferably less than 2.50 weight percent of the soy protein content.

In the past, the downstream processing techniques used in the preparation of soy proteins have included steps that removed and/or destroyed isoflavones. Methods are available today, which provide soy protein products with high, fixed levels of naturally occurring isoflavones. The isoflavones according to the present invention in glucoside and/or aglycone forms can be included in a composition according to the present invention as part of such soy protein products and/or by themselves and/or as part of any other composition comprising isoflavones.

The dietary fibres used in the present invention should preferably comprise a mixture of insoluble fibres and water-soluble fibres also referred to as soluble fibres. Soluble fibres have a lowering effect on blood cholesterol levels. Examples of dietary fibres comprising soluble fibres are fibres from apples, bananas, oranges, carrots, oats, and soybeans. The dietary fibres preferably comprise soluble fibres in an amount of about 5 weight percent, such as about 10 weight percent, for example about 15 weight percent, such as about 20 weight percent, for example about 25 weight percent, such as about 30 weight percent, for example about 35 weight percent, such as about 40 weight percent, for example about 45 weight percent, such as about 50 weight percent, for example about 55 weight percent, such as about 60 weight percent, for example about 65 weight percent, such as about 70 weight percent, for example about 75 weight percent, such as about 80 weight percent, for example about 85 weight percent, such as about 90 weight percent, for example about 95 weight percent. The dietary fibres used in the present invention are preferably soybean fibres, more preferably soy cotyledon fibres. Such fibres are derived from dehulled and defatted soybean cotyledon and are comprised of a mixture of soluble and insoluble fibres. Soy cotyledon fibres are distinctly different from soybean fibres derived from soy hulls as well as other fibre sources. Soy cotyledon fibres are bland tasting, contain no cholesterol, are low in fat and sodium, and they have good water-binding properties and low caloric content.

Soy cotyledon fibres supplied in a fat-modified and low-cholesterol diet are known to further reduce serum cholesterol levels in a subject suffering from mild to severe hypercholesterolemia. The effect is a lowering of the serum levels of total cholesterol including a lowering of LDL-cholesterol. However, HDL-cholesterol and total triglycerides are not significantly affected by soy cotyledon fibres. Soybean fibres, in particular soy cotyledon fibres, are believed to provide a synergistic effect In combination with soy protein and/or with a phytoestrogen compound, such as naturally occurring isoflavones, or to exert a potentiating effect on the soy protein and/or the phytoestrogen compound, said synergistic or potentiating effect being effective in lowering serum lipid and cholesterol levels in subjects having normal as well as elevated serum levels of total cholesterol and total triglycerides.

Without wishing to be bound by any specific theory it is presently believed that both soluble dietary fibres (working as nutrients) and insoluble dietary fibres (working as bulking agents), in particular from soybean fibres, more particularly soy cotyledon fibres, provide favourable growth conditions for the microflora in the human gut, which makes the microflora more effective in deconjugating isoflavones in the glucoside form to the aglycone form. Isoflavones in the aglycone form are absorbed faster and to a greater extent in the human gut than isoflavones in the glucoside form, and isoflavones in the aglycone form are the biologically more active species with regard to lowering lipid serum levels and reducing atherosclerosis. In view hereof it can be understood that administration of a combination of soy proteins, a high, fixed level of isoflavones and a combination of soluble and insoluble fibres is effective in providing an increased uptake of isoflavones.

The amount of dietary fibres of the total weight of a composition according to the present invention on a dry basis is preferably more than 6 weight percent, for example at least 7 weight percent, such as at least 8 weight percent, for example at least 9 weight percent, such as at least 10 weight percent, for example at least 11 weight percent, such as at least 12 weight percent, for example at least 13 weight percent, such as at least 14 weight percent, for example at least 15 weight percent, such as at least 16 weight percent, for example at least 17 weight percent, such as at least 18 weight percent, for example at least 19 weight percent, such as at least 20 weight percent, and preferably less than 50 weight percent Preferred amounts of dietary fibres as a weight percent of the content of soy protein, shall be in the range of from about 10 to 100 weight percent, and preferred amounts are in the range of from 15 to 90 weight percent, such as from 20 to 80 weight percent, for example 25 weight percent, such as 30 weight percent, for example 33 weight percent, such as 35 weight percent, for example 40 weight percent, such as 50 weight percent, for example 60 weight percent, such as 70 weight percent, for example 75 weight percent.

Accordingly, the weight ratio of soy protein to dietary fibres is from about 1.0 to about 10.0, preferably more than about 1.0, for example about 1.25, such as at least about 1.5, for example at least about 1.75, such as at least about 2.0, for example at least about 2.25, such as at least about 2.5, for example at least about 2.75, such as at least about 3.0, for example at least about 3.25, such as at least about 3.5, for example at least about 3.75, such as at least about 4.0, for example at least about 4.25, such as at least about 4.5, for example at least about 4.75, such as at least about 5.0, for example at least about 5.5, such as at least about 6.0, for example at least about 7.5.

The preferred daily dosage of soybean fibres is from at least 1 g to about 100 g soybean fibres, for example from at least 2to about 75 g soybean fibres, such as from at least 3 g to about 50 g, for example from at least 4 g to about 40 g, such as from at least 5 to about 30 g, such as from at least 10 g to about 20 g soybean fibres.

Preferred soy cotyledon fibre products manufactured by Protein Technologies International, Inc. are marketed under the brand name of FIBRIM®. Among the various soybean fibres produced under the FIBRIM® brand, FIBRIM® 1020 is particularly preferred because of a particularly pleasant mouth feel and dispersability for dry blended beverage applications. FIBRIM® 2000 is presently preferred for use in ready made liquids.

Two compositions of isolated soy protein and soy cotyledon fibre are preferred in order to maximise the content of soy protein and isoflavones contained therein namely SUPRO® FXP-HO159 and FIBRIM® 1020 for dry blended beverage applications and SUPRO® FXP-HO159 and FIBRIM® 2000 for use in ready made liquids.

Alternatively, the present invention provides a composition wherein no soy protein is present and wherein the dietary fibres are soy cotyledon fibres. This composition comprises soy cotyledon fibres in an amount of more than 4 weight percent of the total weight of the composition on a dry basis and at least one phytoestrogen compound in an amount of more than 0.10 weight percent of the soy cotyledon fibres of the composition. The present invention also provides the use of such a composition as a medicament and/or in the manufacture of a medicament effective in preventing and/or treating and/or prophylactically treating and/or alleviating and/or eliminating a cardiovascular disease in a subject. The present invention also provides the use of such a composition as a medicament and/or in the manufacture of a medicament effective in preventing and/or treating and/or prophylactically treating and/or alleviating treating, alleviating and/or eliminating arteriosclerosis or a related cardiovascular disease in a subject. The present invention also provides the use of such a composition and/or such a composition for use in treating arteriosclerosis or a related cardiovascular disease in a subject.

When no soy protein is present in the composition, the phytoestrogen compound is preferably present in an amount of at least about 0.12 weight percent of the soy cotyledon fibre content, such as at least about 0.14 weight percent, for example at least about 0.16 weight percent, such as at least about 0.18 weight percent, for example at least about 0.20 weight percent, such as at least about 0.22 weight percent, for example at least about 0.24 weight percent, such as at least about 0.25 weight percent, for example more than about 0.25 weight percent, such as at least about 0.26 weight percent, for example at least about 0.28 weight percent, such as at least about 0.30 weight. percent, for example at least about 0.32 weight percent, such as at least about 0.33 weight percent, for example more than about 0.33 weight percent, such as at least about 0.35 weight percent, for example at least about 0.40 weight percent, such as at least about 0.45 weight percent, for example at least about 0.50 weight percent, such as at least about 0.55 weight percent, for example at least about 0.60 weight percent such as at least about 0.65 weight percent, for example at least about 0.70 weight percent, such as at least about 0.75 weight percent, for example at least about 0.80 weight percent, such as at least about 0.85 weight percent, for example at least about 0.90 weight percent, such as at least about 1.00 weight percent, for example at least about 1.25 weight percent, such as at least about 1.50 weight percent, for example at least about 1.75 weight percent, such as at least about 2.00 weight percent, for example at least about 2.50 weight percent, such as at least about 3.00 weight percent, for example at least about 3.5 weight percent, such as at least about 5.00 weight percent of the soy cotyledon fibre content of the composition, and preferably less than 10.00 weight percent of the soy cotyledon fibre content of the composition.

A composition according to the present invention may optionally comprise a carbohydrate source, a fat source, flavouring agents, vitamins, minerals, electrolytes, trace elements and other conventional additives. The nutritional composition of the present invention may in one embodiment also comprise one or more flavouring agents such as cocoa, vanilla, lime, strawberry or soup flavours, such as mushroom, tomato or bouillon and sweeteners such as aspartame as well as other additives such as xanthan gum.

When a carbohydrate source is present in a composition according to the present invention, it is preferably present in an amount of less than 30 weight percent such as less than 25 weight percent of the composition. Preferably, the amount of carbohydrate amounts to at least 5 weight percent, more preferred at least 10 weight percent, and most preferred at least 15 weight percent, of the composition. The preferred carbohydrates for use in a composition according to the present invention are dextrose, fructose and/or maltodextrin, or glucose. Skimmed milk and lecithinated fat reduced cacao are other possible carbohydrate sources.

When a fat source is present in a composition according to the present invention, it is usually present in an amount from 0.5 to 10 weight percent, preferably 1 to 9 weight percent, such as from 1.5 to 8 weight percent, for example from 2 to 7 weight percent, such as from 2.5 to 6 weight percent of the composition. The fat source will preferably comprise polyunsaturated fatty acids and monounsaturated fatty acids and optionally also saturated fatty acids. Soy lecithins and α-linolenic acid are particularly preferred. The amount of polyunsaturated fatty acids and monounsaturated fatty acids, including the essential fatty acids, may range from 35 to 50, preferably 38 to 44, weight percent of the total amount of the fat source. The essential fatty acids are also called omega-6 and omega-3 fatty acids and include linolic acid and/or linolenic acid (α-linolenic acid). The amount of saturated fatty acids may be from 20 to 30 weight percent, preferably 22 to 26 weight percent, of the total amount of fat.

Vitamins and minerals may optionally be added to a composition according to the present invention in accordance with the limits laid down by health authorities. Preferably, a composition according to the present invention will comprise all recommended vitamins and minerals. The vitamins will typically include A, B1, B2, B12, folic acid, niacin, panthotenic acid, biotin, C, D, E and K. The minerals will typically include iron, zinc, iodine, copper, manganese, chromium and selenium.

Electrolytes, such as sodium, potassium and chlorides, trace elements and other conventional additives may also be added in recommended amounts.

A preferred composition can be obtained by mixing:

|  | Content per 100 gram (%) | Grams per serving |
| --- | --- | --- |
| Isolated soy protein (SUPRO ® FXP-HO159) | 50.00 | 18.5 |
| Soybean fibres (FIBRIM ® 1020) | 12.50 | 4.63 |
| Fructose | 22.62 | 8.37 |
| Lecithinated fat reduced cocoa | 9.30 | 3.44 |
| Soy lecithin | 3.55 | 1.31 |
| Flavourings | 1.28 | 0.47 |
| Xanthan gum | 0.50 | 0.19 |
| Aspartame | 0.25 | 0.09 |

The above-mentioned composition in an amount of preferably about 37 grams corresponds to one serving of a daily diet. The composition has an energy content of about 339 kcal (1,437 kJ) per 100 grams.

A composition according to the present invention may be used for special dietary use, preferably for lowering serum levels of cholesterol and/or LDL-cholesterol and/or triglycerides in hyperlipidemic patients or normocholesterolemic patients suffering from a cardiovascular disease. For example, from one to three daily meals of ordinary food can be supplemented or replaced by a composition according to the present invention. Hereby, significant reductions in serum levels of cholesterol and/or LDL-cholesterol and/or triglycerides can be obtained, as well as an improvement of HDL/LDL-cholesterol ratio and/or an increase in serum HDL-cholesterol levels. The composition may provide from about 50 to about 250 kcal per serving.

The daily dose of a composition according to the present invention may comprise an energy content of from 400 to 800, in particular from 450 to 800 kcal/day, which is considered to be a very low calorie diet (VLCD), or it may comprise an energy content of from 800 to 1200 kcal/day, which is considered to be a low-calorie diet (LCD). In another medical embodiment of the present invention, the energy content may correspond to the daily energy requirement of a normal person.

The present invention also provides a composition according to the invention in the form of a micronutrient. In this connection a micronutrient is a nutritional supplement and/or a pharmacological composition and/or a medicament comprising i) a synthetic phytoestrogen-like compound capable of binding to an estrogen receptor or an estrogen-like receptor, and/or ii) a naturally occurring, plant-extractable compound in an amount, on a weight per weight basis, in excess of the amount of said compound, when it is present in a natural host such as a plant cell from which the compound can be extracted or isolated, and optionally iii) soy peptides obtainable from a partial hydrolysis of soy protein.

The naturally occurring, plant-extractable compound is preferably but not limited to compounds capable of binding to an estrogen receptor, an estrogen-like receptor, a beta-2-adrenergic receptor or a receptor belonging to the class of beta-2-adrenergic receptors. When the naturally occurring compounds are isolated from plants such as soybeans, they may be selected from the group at least containing phytoestrogens such as soybean phytoestrogens such as soybean isoflavones, soy protein or fragments thereof, e.g. peptides or amino acid sequences, soybean fibres, lecithin, linolenic acid, an antioxidant, a saponin, a lignan, a protease inhibitor, a trypsin inhibitor, and a tyrosine kinase inhibitor. Additional constituents of the micronutrient may preferably be selected among a DNA topoisomerase inhibitor, a ribosome kinase inhibitor, a growth control factor such as e.g. epidermal growth factor, transforming growth factor alpha, platelet derived growth factor, and preferably any growth control factor controllable by a tyrosine kinase activity. The micronutrient may also comprise ormeloxifene and/or levormeloxifene as described by among others Holm et al. (1997) in Arteriosclerosis, Thrombosis, and Vascular Biology 17 (10), 2264–2272, and in Clinical Investigation, 100 (4), 821–828. When the naturally occurring compound is an isoflavone the isoflavone may have been, deconjugated to the aglycone form either biologically or in vitro prior to the incorporation in the micronutrient.

In one particularly preferred embodiment the present invention provides a composition or a micronutrient according to the present invention in combination with a functional food ingredient comprising a sterol, preferably an ingredient selected from the group consisting of a stanol ester, a tocotrienol, a mevinolin, and a phytosterol compound such as e.g. campesterol, sitosterol or stigmasterol, or a combination thereof.

According to one preferred embodiment, a composition or a micronutrient according to the present invention is for use as a functional food ingredient. A composition or a micronutrient according to the present invention may also be administered as a probe or by intravenous administration, or in tablet or capsule form. The present invention also provides a pharmaceutical preparation comprising the a composition or a micronutrient according to the present invention, use of the a composition or a micronutrient according to the present invention in therapy and/or a diagnostic method performed on the human or animal body, use of a composition or a micronutrient according to the present invention in the manufacture of a medicament. and use of a composition or a micronutrient according to the present invention in the manufacture of a medicament for treating a subject suffering from cardiovascular diseases.

The micronutrient is particularly useful in preventing and/or treating and/or prophylactically treating and/or alleviating hypercholesterolemia, hypertriglyceridemia, other hyperlipidemias and arteriosclerosis, atherosclerosis and related cardiovascular diseases.

In one embodiment the present invention provides a composition according to the present invention for use as a medicament. A composition according to the present invention for use as a medicament may preferably be used in preventing and/or treating and/or prophylactically treating and/or alleviating cardiovascular diseases such as e.g. a disease selected from the group consisting of arteriosclerosis, atherosclerosis, arteriolosclerosis, coronary heart disease, angina pectoris, thrombosis, myocardial infarction, and hypertension. Arteriosclerosis is a common term for a group of conditions related to the arterial system and leading to an increased arterial wall thickness and a subsequent loss of elasticity. Three main groups of arteriosclerosis frequently referred to are atherosclerosis, Mönckeberg's mediasclerosis and arteriolosclerosis. Atherosclerosis is most frequently observed in the aorta and in the main arteries connected thereto, in the coronary arteries and in the arteries of the brain. Mönckeberg's mediasclerosis leads to a narrowing of the arteries of the extremities, and arteriolosclerosis is related to a narrowing of the small arteries and arterioles caused mainly by hypertension.

The composition according to the present invention is effective in lowering levels of cholesterol in normocholesterolemic patients by at least 2%, for example at least 5%, such as at least 8%, for example at least 10%, such as at least 12%, for example at least 14%, such as at least 16%, for example at least 18%, such as at least 20%, for example at least 25%, such as at least 30%. The composition according to the present invention is effective in lowering levels of triglycerides in normocholesterolemic patients by at least 10%, such as at least 12%, for example at least 14%, such as at least 16%, for example at least 18%, such as at least 20%, for example at least 25%, such as at least 30%.

The composition according to the present invention is effective in lowering levels of cholesterol in mildly hypercholesterolemic patients by at least 3%, for example at least 5%, such as at least 8%, for example at least 10%, such as at least 12%, for example at least 15%, such as at least 20%, for example at least 25%, such as at least 30%, for example at least 35%, such as at least 40%, for example at least 45%. The composition according to the present invention is effective in lowering levels of triglycerides in mildly hypercholesterolemic patients by at least 15%, such as at least 20%, for example at least 25%, such as at least 30%, for example at least 35%, such as at least 40%, for example at least 45%.

The composition according to the present invention is effective in lowering levels of cholesterol in severely hypercholesterolemic patients by at least 3%, for example at least 5%, such as at least 8%, for example at least 10%, such as at least 12%, for example at least 15%, such as at least 20%, for example at least 25%, such as at least 30%, for example at least 35%, such as at least 40%, for example at least 45%, such as at least 50%, for example at least 55%, such as at least 60%. The composition according to the present invention is effective in lowering levels of triglycerides in severely hypercholesterolemic patients by at least 20%, for example at least 25%, such as at least 30%, for example at least 35%, such as at least 40%, for example at least 45%, such as at least 50%, for example at least 55%, such as at least 60%.

A composition according to the present invention for use as a medicament may also be effective in reducing the influx of cholesterol and/or triglycerides into the arterial wall and/or reducing the amount of oxidized LDL-cholesterol present in the arterial wall and/or lowering serum levels, of cholesterol and/or LDL-cholesterol and/or homocystein and/or triglycerides and/or increasing the serum HDL/LDL-cholesterol ratio and/or increasing serum levels of HDL-cholesterol.

In another embodiment the present invention provides the use of a composition according to the present invention in the treatment of cardiovascular diseases e.g. arteriosclerosis. The use of a composition according to the present invention as a medicament and/or in the manufacture of a medicament for treating a subject suffering from cardiovascular diseases represents another embodiment of the present invention. The use of a composition according to the present invention as a medicament and/or in the manufacture of a medicament for treating a subject suffering from arteriosclerosis represents yet another embodiment of the present invention. Such a medicament may e.g. be effective in preventing and/or treating and/or prophylactically treating and/or alleviating e.g. a cardiovascular disease selected from the group consisting of hypercholesterolemia, hypertriglyceridemia, other hyperlipidemias, arteriosclerosis, atherosclerosis, arteriolosclerosis, angina pectoris, thrombosis, myocardial infarction, and hypertension in a subject, where medicaments effective in preventing and/or treating and/or prophylactically treating and/or alleviating arteriosclerosis and/or atherosclerosis in a subject are more preferred. The medicament may also be effective in lowering total serum cholesterol levels and/or LDL-cholesterol levels and/or total serum triglyceride levels and/or total serum levels of homocystein of a subject and/or reducing the influx of cholesterol and/or triglycerides into the arterial wall and/or reducing the amount of oxidized LDL-cholesterol present in the arterial wall. The medicament may also be effective in increasing the serum HDL-LDL-cholesterol ratio of a subject and/or increasing HDL-cholesterol levels of a subject. The medicament may also be effective in preventing, reducing or eliminating fatty streak formation and/or preventing, reducing or eliminating fibrous plaque formation and/or preventing, reducing or eliminating complicated lesion formation. The medicament may also be effective in reducing or eliminating the risk of contracting angina pectoris and/or reducing or eliminating the risk of a subject contracting a myocardial infarction.

The present invention also provides a method of preventing and/or treating and/or prophylactically treating and/or alleviating by therapy a cardiovascular disease in the human or animal body such as an arteriosclerotic, condition of a human or animal body, said method comprising administration of a composition according to the present invention in an amount effective in lowering serum cholesterol levels and/or serum LDL-cholesterol levels and/or serum triglyceride levels and/or serum homocystein levels and/or increasing the serum HDL/LDL-cholesterol ratio and/or serum HDL-cholesterol levels and/or reducing the influx of cholesterol and/or triglycerides into the arterial wall and/or reducing the amount of oxidized LDL-cholesterol present in the arterial wall and/or preventing, reducing or eliminating fatty streak formation and/or preventing, reducing or eliminating fibrous plaque formation and/or preventing, reducing or eliminating complicated lesion formation and/or reducing or eliminating the risk of contracting angina pectoris and/or reducing or eliminating the risk of a subject contracting a myocardial infarction, and/or alleviating the clinical condition of patients contracting a myocardial infection. The cardiovascular disease is preferably a cardiovascular disease selected from the group consisting of hypercholesterolemia, hypertriglyceridemia, other hyperlipidemias, arteriosclerosis, atherosclerosis, arteriolosclerosis, angina pectoris, thrombosis, myocardial infarction, and hypertension and more preferred selected from arteriosclerosis and atherosclerosis.

The period of treatment is preferably in the range of from 1 to 12 months or more, such as from 2 weeks to 9 months, for example from 3 weeks to 6 months, such as from 4 weeks to 4 months, such as from 6 weeks to 3 months. However, the period of treatment shall not be limited to these periods and may e.g. be longer than 12 months, such as e.g. a lifelong treatment in order to prevent cardiovascular diseases.

In one embodiment the present invention provides a pharmaceutical preparation comprising a composition according to the present invention. The pharmaceutical preparation can be prepared in any way known to the skilled person.

In another embodiment the present invention provides the use of a composition according to the present invention as a nutritional preparation and/or in the manufacture of a nutritional preparation for lowering serum cholesterol levels and/or serum LDL-cholesterol levels and/or serum triglyceride levels and/or serum homocystein levels and/or increasing the serum HDL-LDL-cholesterol ratio and/or increasing serum levels of HDL-cholesterol of a subject. The nutritional preparation may take any form, which is suitable for human or animal consumption. In one preferred embodiment, the composition is a powdery mixture, which is suspendable, dispersible or emulsifiable in a liquid for human or animal consumption. The liquid is preferably a water-containing liquid such as e.g. water, coffee, tea or juice. For such a purpose, the composition may be packed in a package intended for covering part of or the total nutritional requirement for a defined period of time. The present invention also provides the nutritional preparation in the form of a dietary supplement.

The nutritional preparation in one embodiment of the present invention is preferably a functional food or drink, i.e. a readily obtainable edible or drinkable substance that is supplemented with a composition according to the present invention to provide a medical or pharmaceutical effect. Accordingly, the present invention provides a composition according to the present invention for use as a functional food ingredient. Functional foods and drinks are preferably selected from the group consisting of diary products, such as yoghurt and yoghurt ice cream, juice, such as orange juice or tomato juice, ready made liquids for drinking, a spreadable product such as e.g. a margarine or a vegetable or plant extracted oil, a cereal product, such as a traditional breakfast cereal product, nutritional bars, biscuits, bread, soups, such as tomato soup, a meat product, such as a hamburger, a meat substitute product, and a vegetable product. In a further embodiment, a nutritional preparation according to the present invention may be in the form of a ready made liquid or in a powder form or in the form of a troche, a solid composition such as a nutritional bar, a fruit bar, a cookie, a cake, a bread or a muffin.

In another embodiment, a composition according to the present invention is a liquid nutritional preparation in a water-containing liquid, in which the solid ingredients are suspended, dispersed or emulgated in an amount of from 10 to 25 weight percent. When the liquid nutritional preparation is intended for drinking, it will usually comprise a flavouring agent as discussed above. However, the liquid nutritional preparation may also be used for probe administration.

In another embodiment, the present invention relates to the use of a composition according to the present invention as a partial or total diet for an overweight subject suffering from an arteriosclerotic condition. Overweight subjects often have an increased serum cholesterol level and increased triglyceride levels and are therefore more likely to develop cardiovascular diseases. However, the present invention is not limited to treating subjects with an increased risk of contracting arteriosclerosis, i.e. subjects likely to have increased serum levels of cholesterol and/or triglycerides. A composition according to the present invention also has substantial serum cholesterol, LDL-cholesterol and serum triglyceride lowering effects in subjects having a more normal lipid profile. The medical use of a composition according to the present invention is not limited to overweight or obese subjects, but may be used for normal weight subjects having increased serum levels of cholesterol and/or LDL-cholesterol and/or triglycerides or for subjects with a cardiovascular condition such as e.g. arteriosclerosis or a related condition who have normal serum levels of cholesterol and/or LDL-cholesterol and/or triglycerides. Such increased serum levels of cholesterol and/or LDL-cholesterol and/or triglycerides may be caused by intake of a diet rich in fats or it may be genetically related.

For the purpose of the present invention, subjects having an initial total serum cholesterol level of 5.7 mmol/l or below are considered to have a normal or hypocholesterolemic level, whereas subjects having a total serum cholesterol level above 5.7 mmol/l are considered to be hypercholesterolemic. Accordingly, by treating normocholesterolemic subjects, it is possible to prevent the development of cardiovascular diseases arising from serum cholesterol levels below a concentration of 5.7 mmol/l in subjects particularly sensitive to developing e.g. arteriosclerosis, or prevent further development of cardiovascular diseases in patients with previous cardiovascular events.

By treating hypercholesterolemic subjects, it is possible to prevent the development of cardiovascular diseases arising from serum cholesterol levels above a concentration of 5.7 mmol/l in subjects sensitive to developing e.g. arteriosclerosis under such conditions.

More particularly, subjects having a total serum cholesterol level of from 5.7 mmol/l to 7.9 mmol/l are considered to be mildly hypercholesterolemic. Accordingly, by treating these hypercholesterolemic subjects, it is possible to prevent the development of cardiovascular diseases arising from serum cholesterol levels of from 5.7 to 7.9 mmol/l. Subjects having a total serum cholesterol level of more than 7.9 mmol/l are considered to be severely hypercholesterolemic. Accordingly, by treating these hypercholesterolemic subjects, it is possible to prevent the development of cardiovascular diseases arising from serum cholesterol levels of more than 7.9 mmol/l.

It has also been shown that a composition according to this invention has a potentiating effect to the effect of medications such as e.g. statins. By combining a composition according to the present invention with e.g. statins, such as HMG-CoA-reductase-inhibitors, bile acid resins, fibrates, nicotinic acid derivatives, oat products, such as oat meal, rye products, such as rye meal and various fish oil concentrates with a high content of ω-3-fatty acids, it is possible to achieve a further 5 to 15% reduction in total cholesterol and/or LDL-cholesterol and/or triglyceride levels. The present invention also provides a combination according to the present invention in combination with a statin, preferably an HMG-CoA-reductase-inhibitor, bile acid resins, fibrates, oat products, rye products, nicotinic acid derivatives and various fish oil concentrates with a high content of ω-3-fatty acids.

EXAMPLE 1

The objective of the present study was to examine if a product comprising isolated soy protein, soybean fibres, and a high, fixed level of isoflavones, is significantly more effective in lowering serum levels of LDL-cholesterol and total cholesterol than placebo. The study was conducted as a randomized, double-blind, placebo controlled trial. Fifty-two patients with a mean baseline cholesterol level of 7.6 mmol/l completed a six-week treatment. Twenty-four consumed a composition according to the invention (Abacor®, Nutri Pharma ASA, Oslo) containing isolated soy protein with high, fixed levels of isoflavones, and soy cotyledon fibres (52 g soy protein, 230 mg soy isoflavones, and 15.5 g soy cotyledon fibres, per day). Twenty-eight consumed a product with the same intakes of protein and fibre, based on casein and cellulose (the placebo). The preparations were given as two daily liquid supplements in addition to the patients regular diets. Both groups were controlled one month after stopping taking the preparations.

The mean reduction of LDL-cholesterol in the Abacor®) treated group after six weeks was 13.1%, whereas it was 7.8% (p=0.014) in the placebo treated group. The reduction of total cholesterol was also larger in the active compared to the placebo group (8.4% vs. 5.1%, p=0.049), without correcting for multiple testing. High-density lipoprotein (HDL) cholesterol showed an increase in both the active and placebo groups (6.2% vs. 5.8%). At the one-month follow-up both groups had returned to pretreatment cholesterol levels.

The results show that intake of a product comprising isolated soy protein with high, fixed levels of isoflavones, and soy cotyledon fibres, significantly reduces serum LDL-cholesterol and total cholesterol, and improves the HDL/LDL-cholesterol ratio. The positive results were achieved in this group of patients after six weeks of treatment.

EXAMPLE 2

The objective of the present study was to examine if a product comprising isolated soy protein, soybean fibres, and a high, fixed level of isoflavones, is significantly more effective in lowering serum levels of LDL-cholesterol, HDL-cholesterol and total cholesterol than placebo. The study was conducted as a randomized, double-blind, placebo controlled trial. 160 patients with plasma levels of LDL-cholesterol ≧4 mM, total cholesterol of 5.8–7.9 mM and triglycerides <4.5 mM completed sixteen weeks treatment. 80 patients divided into two groups of the same size consumed a soy based product (Abacor®, Nutri Pharma ASA, Oslo) containing isolated soy protein with high, fixed levels of isoflavones, and soy cotyledon fibres. Group I (40 patients) received Abacor® I: 18.5 g soy protein (SUPRO® FXP-HO159), 4.63 g soy fibres (FIBRIM® 1020), 3.44 g lecithinated fat reduced cocoa and 1.31 g soy lecithin on a daily basis; Group II (40 patients) received Abacor® II: 31 g soy protein (SUPRO(D FXP-HO159), 7.75 g soy fibres (FIBRIM® 1020), 5.77 g lecithinated fat reduced cocoa and 2.2 g soy lecithin on a daily basis. 80 patients divided into two groups consumed a product with the same intakes of protein and fibre, based on casein, whole milk powder and cellulose (the placebo). The preparations were taken as one daily supplement in addition to the patients' regular diets.

Figure 3:
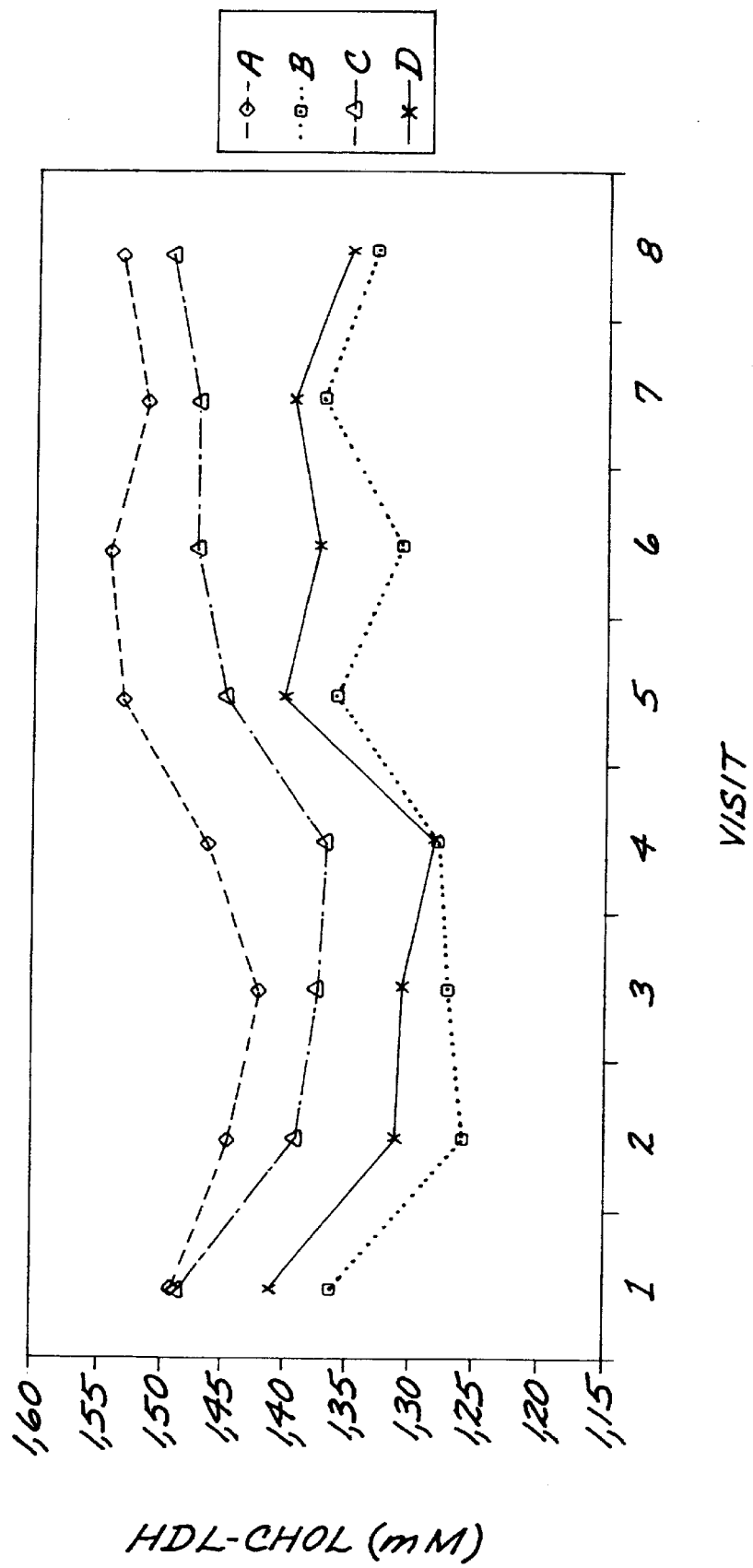
FIG. 3 shows the levels of HDL-cholesterol (mM) for the four groups of patients in Example 2 (A: Patients in Group I; B: Patients receiving placebo with the same intake of protein and fibre as Group I; C: Patients in Group I; D: Patients receiving placebo with the same intake of protein and fibre as Group II) at each of the 8 visits. HDL-chol= HDL-cholesterol.
Figure 4:
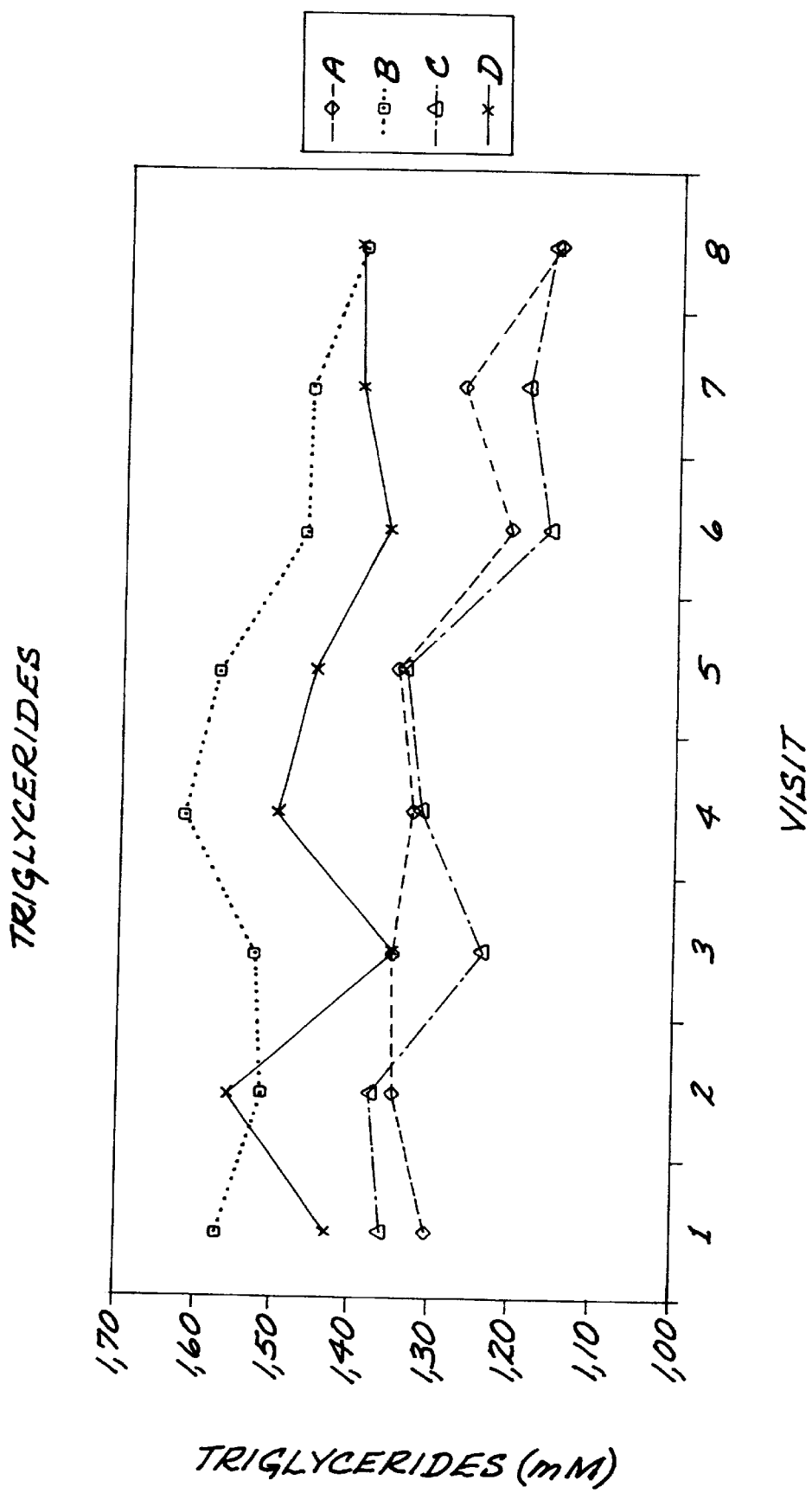
FIG. 4 shows the levels of triglycerides (mM) for the four groups of patients in Example 2 (A: Patients in Group I; B: Patients receiving placebo with the same intake of protein and fibre as Group I; C: Patients in Group I; D: Patients receiving placebo with the same intake of protein and fibre as Group II) at each of the 8 visits.
Figure 5:
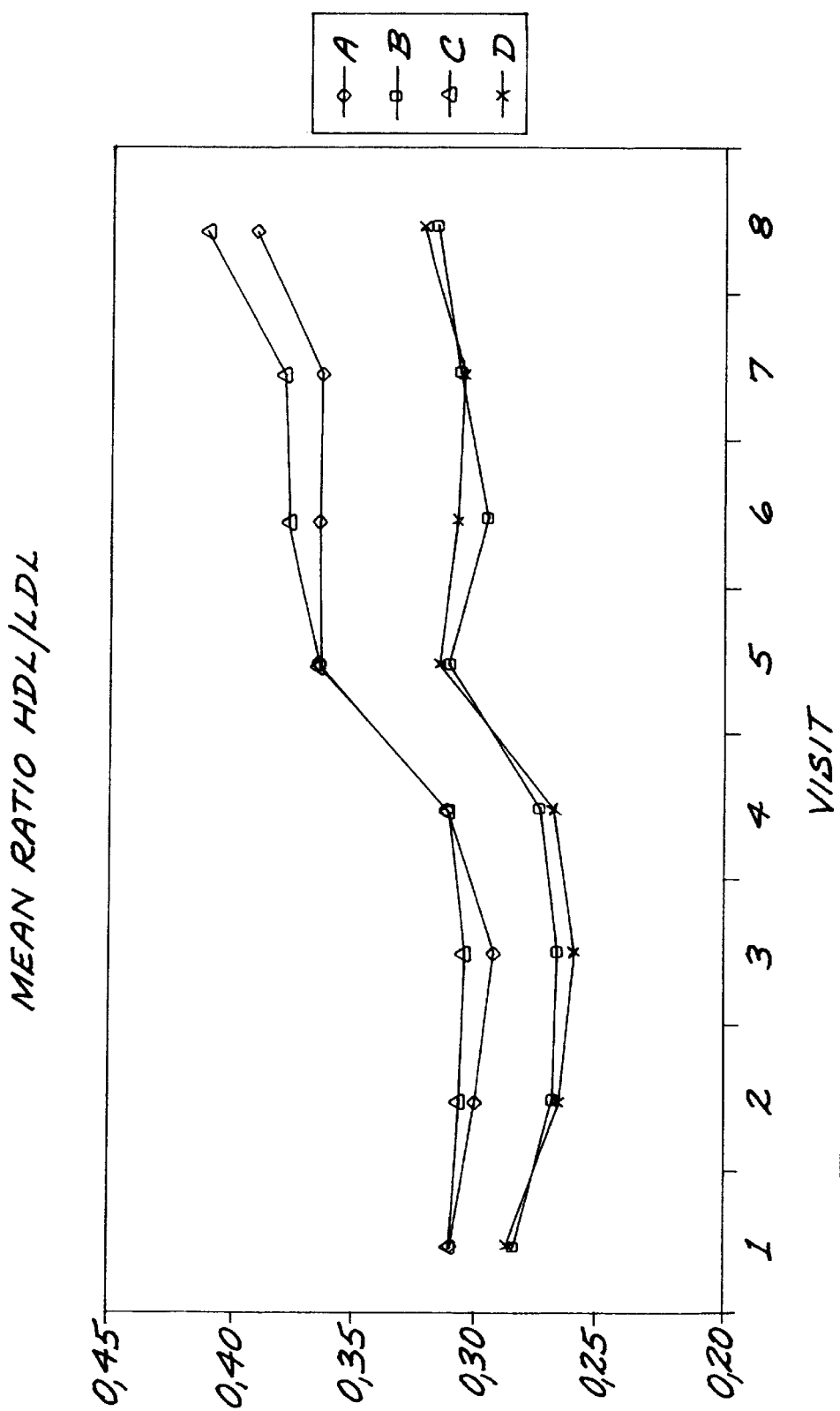
FIG. 5. shows the mean ratio of HDL/LDL-cholesterol for the four groups of patients in Example 2 (A: Patients in Group I; B: Patients receiving placebo with the same intake of protein and fibre as Group I; C: Patients in Group I; D: Patients receiving placebo with the same intake of protein and fibre as Group II) at each of the 8 visits.

The study began with a standardised dietary programme for on average four months for all study participants (visits 1–4, on average during a course of four months) with extensive education in change of diet and dietary instructions. After this, the study participants received Abacor® or placebo as described above (visits 4–8, one month between each). Serum levels of total cholesterol (Table I and FIG. 1), serum levels of LDL-cholesterol (Table II and FIG. 2), serum levels of HDL-cholesterol (Table III and FIG. 3), and serum levels of triglycerides (Table IV and FIG. 4) were measured at all visits during the entire period. The mean ratio of HDL-LDL-cholesterol was also calculated (FIG. 5).

The following designations are used in the following tables.
A: Patients in Group I
B: Patients receiving placebo with the same intake of protein and fibre as Group I
C: Patients in Group II
D: Patients receiving placebo with the same intake of protein and fibre as Group II

TABLE I

Total Cholesterol (mM)

| | Visit 1 | Visit 2 | Visit 3 | Visit 4 | Visit 5 | Visit 6 | Visit 7 | Visit 8 | Change V4–V8 |
|---|---|---|---|---|---|---|---|---|---|
| A | 7.00 | 6.98 | 7.01 | 6.86 | 6.48 | 6.48 | 6.35 | 6.08 | 11.3% |
| B | 6.99 | 6.77 | 6.96 | 6.83 | 6.66 | 6.59 | 6.64 | 6.29 | 8.0% |
| C | 6.91 | 6.61 | 6.54 | 6.46 | 6.18 | 6.01 | 5.95 | 5.71 | 11.7% |
| D | 7.07 | 7.03 | 6.99 | 6.76 | 6.58 | 6.52 | 6.61 | 6.23 | 7.9% |

TABLE II

LDL-cholesterol (mM)

| | Visit 1 | Visit 2 | Visit 3 | Visit 4 | Visit 5 | Visit 6 | Visit 7 | Visit 8 | Change V4–V8 |
|---|---|---|---|---|---|---|---|---|---|
| A | 4.92 | 4.93 | 4.99 | 4.80 | 4.35 | 4.40 | 4.26 | 4.03 | 16.0% |
| B | 4.92 | 4.83 | 5.02 | 4.83 | 4.59 | 4.62 | 4.61 | 4.33 | 10.3% |
| C | 4.80 | 4.60 | 4.61 | 4.53 | 4.13 | 4.03 | 3.92 | 3.71 | 18.2% |
| D | 5.01 | 5.01 | 5.07 | 4.80 | 4.51 | 4.52 | 4.56 | 4.23 | 11.9% |

TABLE III

HDL-cholesterol (mM)

| | Visit 1 | Visit 2 | Visit 3 | Visit 4 | Visit 5 | Visit 6 | Visit 7 | Visit 8 | Change V4–V8 |
|---|---|---|---|---|---|---|---|---|---|
| A | 1.49 | 1.44 | 1.42 | 1.46 | 1.53 | 1.54 | 1.52 | 1.54 | −5.0% |
| B | 1.36 | 1.26 | 1.27 | 1.28 | 1.36 | 1.31 | 1.37 | 1.33 | −4.2% |
| C | 1.49 | 1.39 | 1.37 | 1.37 | 1.45 | 1.47 | 1.47 | 1.50 | −9.5% |
| D | 1.41 | 1.31 | 1.31 | 1.28 | 1.40 | 1.37 | 1.40 | 1.35 | −5.4% |

TABLE IV

Triglycerides (mM)

| | Visit 1 | Visit 2 | Visit 3 | Visit 4 | Visit 5 | Visit 6 | Visit 7 | Visit 8 | Change V4–V8 |
|---|---|---|---|---|---|---|---|---|---|
| A | 1.30 | 1.34 | 1.35 | 1.32 | 1.34 | 1.21 | 1.27 | 1.15 | 13.1% |
| B | 1.57 | 1.52 | 1.53 | 1.62 | 1.58 | 1.47 | 1.46 | 1.39 | 13.9% |
| C | 1.36 | 1.37 | 1.24 | 1.31 | 1.34 | 1.16 | 1.19 | 1.16 | 11.9% |
| D | 1.43 | 1.56 | 1.34 | 1.50 | 1.45 | 1.36 | 1.40 | 1.40 | 6.6% |

These results show, that intake of a composition according to the invention in the aforesaid amounts reduces serum levels of total cholesterol with more than 11% for Abacor® I and Abacor® II (Table I and FIG. 1). More remarkably, intake of a composition according to the invention reduces serum levels of LDL-cholesterol with 18.2% for Abacor® II after an initial reduction of about 5% due to change of diet resulting. in a total reduction of LDL-cholesterol of about 23% with intake of a composition according to the invention and change of diet (Table II and FIG. 2). This is among the biggest reductions in serum levels of LDL-cholesterol observed with foodstuffs. Surprisingly, intake of Abacor® I (having only 60% of the protein content of Abacor® II) reduces serum levels of LDL-cholesterol with 16.0% after the initial reduction, which is quite close to the. result observed with Abacor® II. The results further show, that serum levels of HDL-cholesterol is increased with about 10% for Abacor® II (Table III and FIG. 3), that the serum levels of triglycerides is reduced with more than 10% for both Abacor® I and Abacor® II (Table IV and FIG. 4), and that the HDL-LDL-ratio is improved with about 33% for Abacor® II and with about 25% for Abacor® I (FIG. 5).

Figure 2:
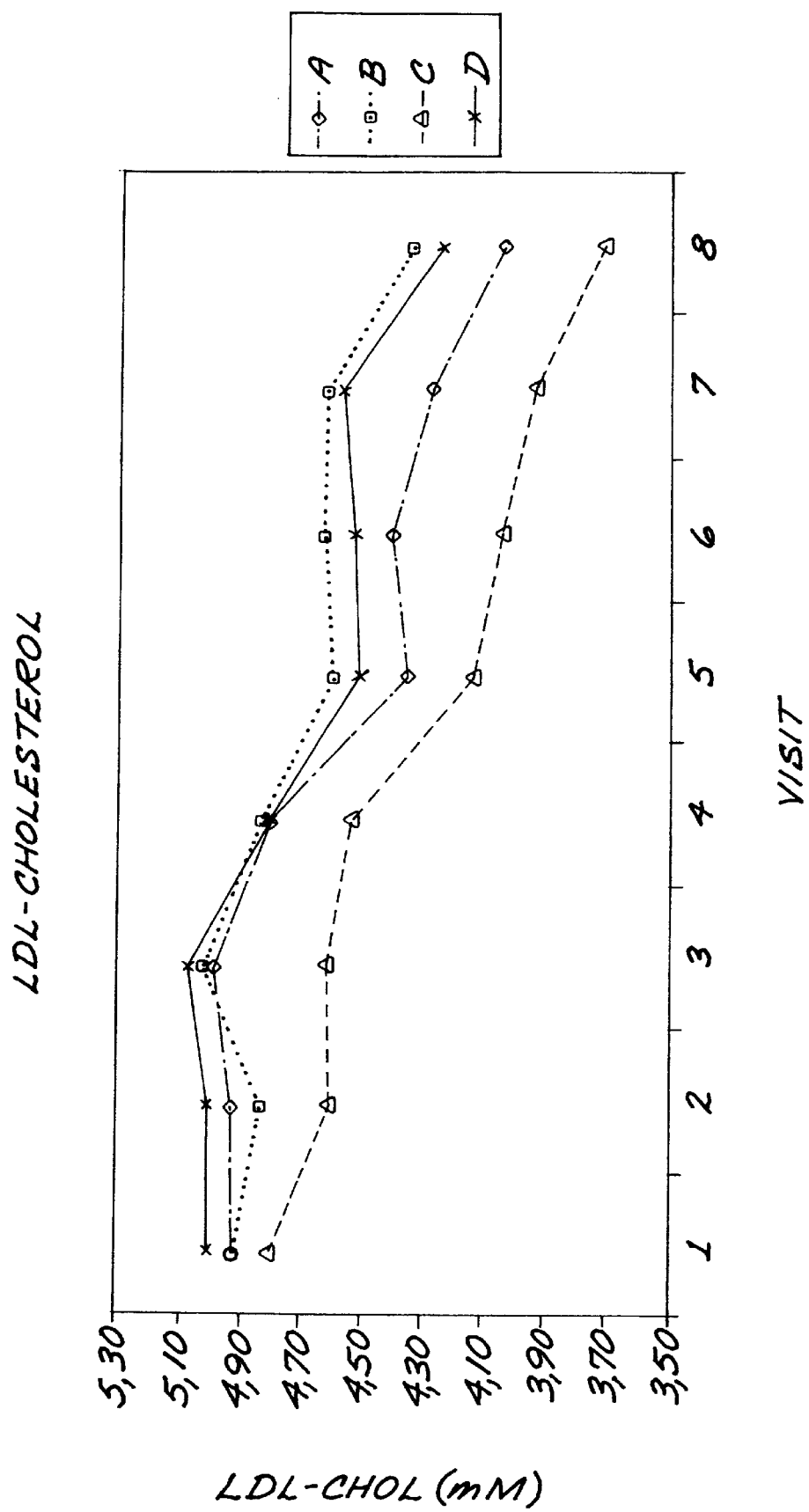
FIG. 2 shows the levels of LDL-cholesterol (mM) for the four groups of patients in Example 2 (A: Patients in Group I; B: Patients receiving placebo with the same intake of protein and fibre as Group I; C: Patients in Group I; D: Patients receiving placebo with the same intake of protein and, fibre as Group II) at each of the 8 visits. LDL-chol= LDL-cholesterol.

Surprisingly, the reduction of cholesterol levels caused by the continued use of Abacor® does not stop after approximately one month, as could be expected since the turn-over of cholesterol in the body is 2 to 3 weeks, but the levels of cholesterol are continually reduced over a period of four months (see FIGS. 1 and 2).

What is claimed is:

1. A composition comprising:
   (a) a soy protein source, selected from the group consisting of isolated soy protein, soy protein concentrate and soy flour, said soy protein source providing an amount of soy protein, which is at least 45 weight percent of the total protein content of the composition, said total protein content providing at least 15 percent of the total energy content of the composition,
   (b) at least one phytoestrogen compound in an amount of more than 0.16 weight percent of the soy protein content of the composition, and
   (c) dietary fibres in an amount of more than 6 weight percent of the total weight of the composition on a dry basis.

2. A composition according to claim 1, wherein the soy protein source is isolated soy protein and the amount of isolated soy protein is at least 50 weight percent of the total protein content.

3. A composition according to claim 2, wherein the amount of isolated soy protein is at least 75 weight percent of the total protein content.

4. A composition according to claim 3, wherein the amount of isolated soy protein is at least 90 weight percent of the total protein content.

5. A composition according to claim 4, wherein all of the protein is isolated soy protein.

6. A composition according to claim 1, wherein the soy protein source is soy protein concentrate or soy flour and the amount of soy protein is at least 50 weight percent of the total protein content.

7. A composition according to claim 6, wherein the amount of soy protein is at least 75 weight percent of the total protein content.

8. A composition according to claim 7, wherein the amount of soy protein is at least 90 weight percent of the total protein content.

9. A composition according to claim 8, wherein all of the protein is soy protein.

10. A composition according to claim 1 wherein the dietary fibres are soybean fibres.

11. A composition according to claim 10, wherein the soybean fibres are soy cotyledon fibres.

12. A composition according to claim 1 wherein the phytoestrogen compound is selected among isoflavones.

13. A composition according to claim 12 wherein the isoflavones are selected from the group consisting of genistein, daidzein, glycitein and equol.

14. A composition according to claim 13 wherein the isoflavones are genistein and/or daidzein.

15. A composition according to claim 14 wherein the isoflavone is genistein.

16. A composition according to claim 12 wherein the isoflavones are in the aglycone form.

17. A composition according to claim 1 wherein the dietary fibres are present in an amount of at least 7 weight percent of the composition.

18. A composition according to claim 1 wherein the weight ratio of soy protein to dietary fibres is at least about 1.0.

19. A composition according to claim 18 wherein the weight ratio of soy protein to dietary fibres is at least about 1.5.

20. A composition according to claim 19 wherein the weight ratio of soy protein to dietary fibres is at least about 2.0.

21. A composition according to claim 20 wherein the weight ratio of soy protein to dietary fibres is at least about 2.5.

22. A composition according to claim 21 wherein the weight ratio of soy protein to dietary fibres is at least about 3.0.

23. A composition according to claim 22 wherein the weight ratio of soy protein to dietary fibres is at least about 4.0.

24. A composition according to claim 23 wherein the weight ratio of soy protein to dietary fibres is at least about 5.0.

25. A composition according to claim 1 additionally comprising one or more of the components selected from the group consisting of statins, bile acid resins, fibrates, nicotinic acid derivatives, oat products, rye products and fish oil concentrates with a high content of omaga-3-fatty acids.

26. A composition according to claim 25 wherein the statins are selected among beta-hydroxy-beta-methylglutaryl coenzyme A (HMG-CoA) reductase inhibitors.

27. A composition according to claim 1 further comprising an additional component selected from an additional protein source, an additional carbohydrate source and an additional fat source.

28. A composition according to claim 27 wherein the additional fat source is a soy lecithin.

29. A composition according to claim 27 wherein the additional fat source is selected from the group consisting of polyunsaturated and monounsaturated fatty acids.

30. A composition according to claim 1 forming a micronutrient.

31. A composition according to claim 30 comprising an additional component selected from the group consisting of a deoxyribonucleic acid (DNA) topoisomerase inhibitor, a ribosome kinase inhibitor and a growth control factor.

32. A composition according to claim 31 wherein the growth control factor is a growth control factor controllable by a tyrosine kinase activity.

33. A composition according to claim 30 additionally comprising ormeloxifene or levormeloxifene.

34. A composition according to claim 1 in combination with a functional food ingredient comprising a sterol.

35. A composition according to claim 34 wherein the sterol is selected from the group consisting of a stanol ester, a tocotrienol, a mevinolin, and a phytosterol compound.

36. A composition according to claim 1 adapted in form of administration for use as a functional food ingredient.

37. A composition according to claim 36 where the functional food is selected from the group consisting of dairy products, juice, ready made liquids for drinking, a spreadable product, a cereal product, nutritional bars, biscuits, bread, soups, meat products, meat substitute products, and a vegetable product.

38. A composition according to claim 1 adapted in formulation for special dietary use.

39. A composition according to claim 38 adapted in formulation for lowering serum levels of one of total cholesterol, low density lipoprotein-cholesterol (LDL-cholesterol) and triglycerides or combinations thereof in a subject.

40. A composition according to claim 38 adapted in formulation for lowering serum levels of one of total cholesterol, low density lipoprotein-cholesterol (LDL-cholesterol) and triglycerides or combinations thereof in hyperlipidemic patients or in normocholesterolemic patients suffering from a cardiovascular disease.

41. A composition according to claim 1 adapted in formulation for use as a medicament.

42. A composition according to claim 41 adapted in formulation for use in lowering serum levels of one of homocystein, total cholesterol, low density lipoprotein-cholesterol (LDL-cholesterol) and triglycerides or any combinations thereof, or adapted in formulation for reducing the influx of cholesterol or of triglycerides into the arterial wall or adapted for increasing the serum high density lipoprotein/low density lipoprotein (HDL/LDL) cholesterol ratio or of the serum high density lipoprotein (HDL)-cholesterol level of a subject.

43. A pharmaceutical preparation comprising a composition according to claim 1.

44. A pharmaceutical preparation according to claim 43 wherein the preparation is effective in lowering one of total serum cholesterol levels, serum LDL-cholesterol levels, serum triglyceride levels and serum levels of homocystein of a subject or any combinations thereof, or is effective for increasing the serum HDL/LDL-cholesterol ratio or serum HDL-cholesterol levels of a subject.

45. A composition contained in a nutritional preparation according to claim 1 adapted in formulation for lowering one of total serum cholesterol levels, serum LDL cholesterol levels, serum triglyceride levels and serum homocystein levels or any combinations thereof, or adapted in formulation for increasing the HDL/LDL-cholesterol ratio or serum HDL-cholesterol levels of a subject.

46. A composition according to claim 45 wherein the nutritional preparation forms a dietary supplement.

* * * * *

UNITED STATES PATENT AND TRADEMARK OFFICE
CERTIFICATE OF CORRECTION

PATENT NO. : 6,630,178 B1
DATED : October 7, 2003
INVENTOR(S) : Lars Henrik Hóie It is certified that error appears in the above-identified patent and that said Letters Patent is hereby corrected as shown below:

Column 4,
Line 60, "importantly" should be -- Importantly --
Line 62, "-200 mg per deciliter of serum may" should be -- "-200 mg per deciliter of serum– may --

Column 7,
Line 3, "proteins. the" should be -- proteins. The --
Line 24, "remains to, determine" should be -- remains to determine --
Line 28, "when, long-term" should be -- when long term --

Column 8,
Line 35, "Potter (Am. J. Clin. Nutr. 5, 501-506 (1993))" should be -- Potter (Am. J. Clin. Nutr. 58, 501-506 (1993)) --

Column 9,
Line 34, "WO 95/lb529" should be -- WO 95/10529 --

Column 11,
Line 52, "equivalent, The" should be -- equivalent. The --
Line 63, "may be Included in" should be -- may be included in --

Column 12,
Line 5, "effect, Dietary fibres," should be -- effect. Dietary fibres, --
Line 28, "at least percent of" should be -- at least 15 percent of --
Lines 33-34, "more than 6 weight percent" should be -- more than 4 weight percent --
Line 41, "at least percent of" should be -- at least 15 percent of --
Line 55, "equal" should be --equol --

Column 18,
Line 44, "at least 56 weight percent" should be -- at least 80 weight percent --
Line 65, "17P-estradiol" should be -- 17β-estradiol --

Column 19,
Lines 8-9, "present Invention" should be -- present invention --
Lines 10 and 12, "equal" should be -- equol --
Line 21, "included In" should be -- included in --

UNITED STATES PATENT AND TRADEMARK OFFICE
CERTIFICATE OF CORRECTION

PATENT NO. : 6,630,178 B1
DATED : October 7, 2003
INVENTOR(S) : Lars Henrik Höie It is certified that error appears in the above-identified patent and that said Letters Patent is hereby corrected as shown below:

Column 20,
Line 27, "effect In" should be -- effect in --

Column 21,
Line 22, "2to" should be -- 2 to --

Column 22,
Line 5, "0.30 weight. percent," should be -- 0.30 weight percent, --

Column 24,
Line 19, "been, deconjugated" should be -- been deconjugated --

Column 26,
Line 29, "arteriosclerotic, condition" should be -- arteriosclerotic condition --
Line 57, "from6 weeks" should be -- from 6 weeks --

Column 27,
Line 5, "HDL-LDL-cholesterol ratio" should be -- HDL/LDL-cholesterol ratio --

Column 29,
Line 59, "HDL-LDL-cholesterol" should be -- HDL/LDL-cholesterol --

Column 30,
Line 60, "the. result" should be -- the result --

Signed and Sealed this

Third Day of August, 2004

JON W. DUDAS
*Acting Director of the United States Patent and Trademark Office*